(12) United States Patent
Flick

(10) Patent No.: US 7,291,762 B2
(45) Date of Patent: Nov. 6, 2007

(54) MULTILAYER CONDUCTIVE APPLIANCE HAVING WOUND HEALING AND ANALGESIC PROPERTIES

(75) Inventor: A. Bart Flick, Lakemont, GA (US)

(73) Assignee: Argentum International, LLC, Lakemont, GA (US)

( * ) Notice: Subject to any disclaimer, the term of this patent is extended or adjusted under 35 U.S.C. 154(b) by 172 days.

(21) Appl. No.: 10/660,209

(22) Filed: Sep. 11, 2003

(65) Prior Publication Data

US 2004/0049145 A1    Mar. 11, 2004

Related U.S. Application Data

(63) Continuation of application No. 09/531,245, filed on Mar. 21, 2000, now Pat. No. 6,861,570, which is a continuation of application No. PCT/US98/19689, filed on Sep. 22, 1998.

(51) Int. Cl.
*A61F 13/00* (2006.01)
*A61F 15/00* (2006.01)
*A61L 15/00* (2006.01)

(52) U.S. Cl. ............... 602/48; 604/304; 424/443; 424/445

(58) Field of Classification Search ............ 602/41–59; 604/304–308; 424/443–449; 128/888, 889
See application file for complete search history.

(56) References Cited

U.S. PATENT DOCUMENTS 1,498,059 A    6/1924    Tyler (Continued)

FOREIGN PATENT DOCUMENTS

EP    0 099 758    2/1984

(Continued)

OTHER PUBLICATIONS

U.S. Appl. No. 08/707,779, filed Sep. 3, 1996, Becker et al.

(Continued)

*Primary Examiner*—Patricia Bianco
*Assistant Examiner*—Kiandra C. Lewis
(74) *Attorney, Agent, or Firm*—Pabst Patent Group LLP

(57) ABSTRACT

A dressing for promoting healing and pain relief of the body of a living organism having a pathologic condition has at least one layer of conductive material having a resistance no greater than 1000 $\Omega/cm^2$. When placed proximate a portion of the body of the living organism suffering from the pathologic condition, the dressing alters the electrodynamic processes occurring in conjunction with said pathologic condition to promote healing and pain relief in the living organism. When used as a wound dressing, the conductive material is placed in contact with tissue around the periphery of the wound and with the wound, lowering the electrical potential and resistance of the wound and increasing the wound current. In an exemplary embodiment, the conductive material is a multi-ply nylon fabric plated with silver by an autocatalytic electroless plating process and with the plies in electrical continuity. The dressing provides an antimicrobial and analgesic effect. The dressing may be provided for numerous applications and may include other layers such as an absorbent layer, a semi-permeable layer and additional layer of conductor material. Multilaminate embodiments of the present invention exhibit conductive material concentration gradients and, potentially, a capacitive effect when sequential conductor layers are insulated by intervening layers.

7 Claims, 28 Drawing Sheets

U.S. PATENT DOCUMENTS

| | | | |
|---|---|---|---|
| 1,545,413 A | 7/1925 | Elmvall | |
| 1,975,518 A | 10/1934 | Rose | |
| 1,989,282 A | 1/1935 | Kimble et al. | |
| 2,934,066 A | 4/1960 | Stowasser | 128/156 |
| 3,326,213 A | 6/1967 | Gallagher | 128/156 |
| 3,420,233 A | 1/1969 | Kanof | 128/260 |
| 3,543,760 A | 12/1970 | Bolduc | |
| 3,596,657 A | 8/1971 | Eidus | 128/156 |
| 3,799,162 A | 3/1974 | Romero-Sierra et al. | |
| 3,800,792 A | 4/1974 | McKnight et al. | 128/156 |
| 3,817,253 A | 6/1974 | Gonser | |
| 3,830,908 A | 8/1974 | Klippel et al. | 424/28 |
| 3,845,771 A | 11/1974 | Vise | |
| 3,911,906 A | 10/1975 | Reinhold, Jr. | |
| 3,914,488 A | 10/1975 | Gorrafa et al. | |
| 3,934,066 A | 1/1976 | Murch | 428/248 |
| 3,964,477 A | 6/1976 | Ellis et al. | 128/172.1 |
| 4,027,393 A | 6/1977 | Ellis et al. | 32/10 A |
| 4,034,750 A | 7/1977 | Seiderman | 128/155 |
| 4,142,521 A | 3/1979 | Konikoff | 128/82.1 |
| 4,213,463 A | 7/1980 | Osenkarski | |
| 4,240,437 A | 12/1980 | Church | |
| 4,291,125 A | 9/1981 | Greatbatch | 435/240 |
| 4,297,995 A | 11/1981 | Golub | 128/156 |
| 4,312,340 A | 1/1982 | Donadelli | |
| 4,313,438 A | 2/1982 | Greatbatch | 128/207.21 |
| 4,333,449 A | 6/1982 | Muller et al. | |
| 4,456,001 A | 6/1984 | Pescatore | |
| 4,476,590 A | 10/1984 | Scales et al. | 3/1.91 |
| 4,486,488 A | 12/1984 | Pietsch et al. | |
| 4,509,535 A | 4/1985 | Bryan | |
| 4,510,939 A | 4/1985 | Brenman et al. | |
| 4,528,265 A | 7/1985 | Becker | 435/172.1 |
| 4,529,623 A | 7/1985 | Maggs | 427/227 |
| 4,541,426 A | 9/1985 | Webster | 128/156 |
| 4,551,139 A | 11/1985 | Plaas et al. | 604/290 |
| 4,554,923 A | 11/1985 | Batters | |
| 4,556,051 A | 12/1985 | Maurer | |
| 4,563,184 A | 1/1986 | Korol | 604/368 |
| 4,600,001 A | 7/1986 | Gilman | 128/156 |
| 4,606,338 A | 8/1986 | Greenway et al. | 128/156 |
| 4,615,705 A | 10/1986 | Scales et al. | 623/11 |
| 4,619,252 A | 10/1986 | Ibbott | 128/82.1 |
| 4,635,624 A | 1/1987 | Gilman | 128/156 |
| 4,646,730 A | 3/1987 | Schonfeld et al. | 728/156 |
| 4,654,323 A | 3/1987 | Beitner | |
| 4,664,118 A | 5/1987 | Batters | |
| 4,671,266 A | 6/1987 | Lengyel et al. | 128/156 |
| 4,728,323 A | 3/1988 | Matson | 604/304 |
| 4,747,845 A | 5/1988 | Korol | 604/368 |
| 4,757,804 A | 7/1988 | Griffith et al. | 128/1.5 |
| 4,767,401 A * | 8/1988 | Seiderman | 604/20 |
| 4,781,705 A | 11/1988 | Shepherd et al. | 604/289 |
| 4,798,603 A | 1/1989 | Meyer et al. | 604/378 |
| 4,817,594 A | 4/1989 | Juhasz | 128/155 |
| 4,818,697 A | 4/1989 | Liboff et al. | 435/173 |
| 4,825,877 A | 5/1989 | Kempe | 128/846 |
| 4,847,049 A | 7/1989 | Yamamoto | 422/24 |
| 4,867,166 A | 9/1989 | Axelgaard et al. | |
| 4,886,505 A | 12/1989 | Haynes et al. | 604/265 |
| 4,889,530 A | 12/1989 | Smith | 604/304 |
| 4,909,244 A | 3/1990 | Quarfoot | 128/156 |
| 4,911,688 A | 3/1990 | Jones | 604/20 |
| 4,932,951 A | 6/1990 | Liboff et al. | 606/13 |
| 4,935,087 A | 6/1990 | Gilman | 156/251 |
| 4,937,323 A | 6/1990 | Silver et al. | |
| 4,960,413 A | 10/1990 | Sagar et al. | 604/289 |
| 4,979,946 A | 12/1990 | Gilman | 604/307 |
| 4,982,742 A | 1/1991 | Claude | |
| 4,984,570 A | 1/1991 | Langen et al. | 128/156 |
| 4,990,144 A | 2/1991 | Blott | 604/304 |
| 4,997,425 A | 3/1991 | Shioya et al. | 604/304 |
| 5,018,515 A | 5/1991 | Gilman | 128/155 |
| 5,018,516 A | 5/1991 | Gilman | 128/155 |
| 5,019,096 A | 5/1991 | Fox, Jr. et al. | |
| 5,038,797 A | 8/1991 | Batters | |
| 5,042,466 A | 8/1991 | McKnight | 128/155 |
| 5,049,139 A | 9/1991 | Gilchrist | 604/265 |
| 5,056,510 A | 10/1991 | Gilman | 128/155 |
| 5,067,478 A | 11/1991 | Berlant | |
| 5,130,342 A | 7/1992 | McAllister et al. | |
| 5,133,199 A | 7/1992 | Parikh et al. | 66/192 |
| 5,147,338 A | 9/1992 | Lang et al. | 604/304 |
| 5,147,344 A | 9/1992 | Sachau et al. | |
| 5,158,555 A | 10/1992 | Porzilli | 604/307 |
| 5,167,613 A | 12/1992 | Karami et al. | 602/42 |
| 5,180,585 A | 1/1993 | Jacobson et al. | |
| 5,185,000 A | 2/1993 | Brandt et al. | |
| 5,266,371 A | 11/1993 | Sugii et al. | 428/40 |
| 5,288,544 A | 2/1994 | Mallen et al. | |
| 5,292,589 A | 3/1994 | Shepherd et al. | 428/412 |
| 5,306,229 A | 4/1994 | Brandt et al. | |
| 5,308,313 A | 5/1994 | Karami et al. | 602/55 |
| 5,320,908 A | 6/1994 | Sodervall et al. | |
| 5,322,520 A | 6/1994 | Milder | 604/265 |
| 5,324,275 A | 6/1994 | Raad et al. | 604/265 |
| 5,326,567 A | 7/1994 | Capelli | |
| 5,333,753 A | 8/1994 | Etheredge | 221/33 |
| 5,340,363 A | 8/1994 | Fabo | 604/304 |
| 5,374,283 A | 12/1994 | Flick | 607/46 |
| 5,395,398 A * | 3/1995 | Rogozinski | 607/50 |
| 5,405,644 A | 4/1995 | Ohsumi et al. | |
| 5,413,788 A | 5/1995 | Edwards et al. | |
| 5,419,161 A | 5/1995 | Bodenschatz et al. | |
| 5,429,590 A | 7/1995 | Saito et al. | 602/48 |
| 5,429,591 A | 7/1995 | Yamamoto et al. | 602/54 |
| 5,433,987 A | 7/1995 | Peterson et al. | |
| 5,454,886 A | 10/1995 | Burrell et al. | 148/565 |
| 5,465,735 A | 11/1995 | Patel | 128/888 |
| 5,470,576 A | 11/1995 | Patel | 424/445 |
| 5,470,585 A | 11/1995 | Gilchrist | 424/604 |
| 5,512,041 A | 4/1996 | Bogart | 602/58 |
| 5,520,664 A | 5/1996 | Bricault et al. | 604/265 |
| 5,543,151 A | 8/1996 | Shirai et al. | 424/448 |
| 5,571,079 A | 11/1996 | Bello et al. | 602/46 |
| 5,571,521 A | 11/1996 | Lasker | 424/409 |
| 5,595,750 A | 1/1997 | Jacobson et al. | |
| 5,607,683 A | 3/1997 | Capelli | 424/405 |
| 5,632,731 A | 5/1997 | Patel | 602/59 |
| 5,662,913 A | 9/1997 | Capelli | |
| 5,681,575 A | 10/1997 | Burrell et al. | 424/423 |
| 5,695,857 A | 12/1997 | Burrell et al. | 428/209 |
| 5,744,151 A | 4/1998 | Capelli | |
| 5,753,251 A | 5/1998 | Burrell et al. | 424/426 |
| 5,770,255 A | 6/1998 | Burrell et al. | 427/2.1 |
| 5,772,620 A | 6/1998 | Szlema et al. | |
| 5,779,659 A | 7/1998 | Allen | 602/75 |
| 5,782,785 A | 7/1998 | Herzberg | |
| 5,782,788 A | 7/1998 | Widemire | 602/48 |
| 5,814,094 A | 9/1998 | Becker et al. | 607/50 |
| 5,824,267 A | 10/1998 | Kawasumi et al. | |
| 5,836,970 A | 11/1998 | Pandit | 606/213 |
| 5,844,013 A | 12/1998 | Kenndoff et al. | |
| 5,921,948 A | 7/1999 | Kawaguchi et al. | 602/52 |
| 5,974,344 A | 10/1999 | Shoemaker, II | 607/149 |
| 5,985,301 A | 11/1999 | Nakamura et al. | |
| 5,985,308 A | 11/1999 | Burrell et al. | |
| 5,998,692 A | 12/1999 | Gilding | |
| 6,004,667 A | 12/1999 | Sakurada et al. | 428/323 |
| 6,014,585 A | 1/2000 | Stoddard | |
| 6,063,980 A | 5/2000 | Peterson et al. | |
| 6,074,965 A | 6/2000 | Bodenschatz et al. | |
| 6,087,549 A | 7/2000 | Flick | 602/41 |
| 6,093,414 A | 7/2000 | Capelli | |

| | | |
|---|---|---|
| 6,099,489 A | 8/2000 | Herzberg et al. |
| 6,120,470 A | 9/2000 | Bodenschatz et al. |
| 6,129,694 A | 10/2000 | Bodenschatz |
| 6,139,856 A | 10/2000 | Kaminska et al. .......... 424/404 |
| 6,149,616 A | 11/2000 | Szlema et al. |
| 6,160,196 A | 12/2000 | Knieler et al. |
| 6,171,648 B1 | 1/2001 | Himmelsbach et al. |
| 6,180,544 B1 | 1/2001 | Jauchen et al. |
| 6,190,407 B1 | 2/2001 | Ogle et al. |
| 6,191,337 B1 | 2/2001 | Himmelsbach |
| 6,210,704 B1 | 4/2001 | Sasaki et al. ............... 424/443 |
| 6,224,898 B1 | 5/2001 | Balogh et al. |
| 6,224,983 B1 | 5/2001 | Sodervall et al. |
| 6,245,959 B1 | 6/2001 | Ohira et al. .................. 602/41 |
| 6,248,932 B1 | 6/2001 | Himmelsbach |
| 6,267,743 B1 | 7/2001 | Bodenschatz et al. |
| 6,267,782 B1 | 7/2001 | Ogle et al. |
| 6,274,205 B1 | 8/2001 | Himmelsbach et al. |
| 6,284,328 B1 | 9/2001 | Leydecker et al. |
| 6,322,588 B1 | 11/2001 | Ogle et al. |
| 6,333,093 B1 | 12/2001 | Burrell et al. |
| 6,348,212 B2 | 2/2002 | Hymes et al. |
| 6,350,247 B2 | 2/2002 | Bodenschatz et al. |
| 6,355,858 B1 | 3/2002 | Gibbins |
| 6,383,630 B1 | 5/2002 | Jauchen et al. |
| 6,428,800 B2 | 8/2002 | Greenspan et al. |
| 6,436,420 B1 | 8/2002 | Antelman |
| 6,447,470 B2 | 9/2002 | Bodenschatz et al. |
| 6,459,013 B1 | 10/2002 | Himmelsbach |
| 6,495,230 B1 | 12/2002 | do Canto |
| 6,506,957 B1 | 1/2003 | Himmelsbach et al. |
| 6,524,699 B1 | 2/2003 | Himmelsbach et al. |
| 6,551,704 B2 | 4/2003 | Himmelsbach et al. |
| 6,555,730 B1 | 4/2003 | Albrod et al. |
| 6,569,111 B2 | 5/2003 | Herzberg |
| 6,579,539 B2 | 6/2003 | Terry et al. |
| 6,582,713 B2 | 6/2003 | Newll et al. |
| 6,592,888 B1 | 7/2003 | Jensen et al. |
| 6,599,525 B2 | 7/2003 | Scamilla Aledo et al. |
| 6,605,751 B1 | 8/2003 | Gibbins et al. |
| 6,617,485 B2 | 9/2003 | Herzberg |
| 6,656,491 B1 | 12/2003 | Brosck et al. |
| 6,695,824 B2 | 2/2004 | Howard et al. |
| 6,706,279 B1 | 3/2004 | Hazzi |
| 6,713,659 B2 | 3/2004 | Bodenschatz et al. |
| 6,716,895 B1 | 4/2004 | Terry |
| 6,730,053 B1 | 5/2004 | Bodenschatz et al. |
| 6,822,132 B2 | 11/2004 | Ahrens et al. |
| 6,852,366 B2 | 2/2005 | Zschaeck |
| 6,861,570 B1 | 3/2005 | Flick |
| 6,897,349 B2 | 5/2005 | Gibbins et al. |
| 7,005,556 B1 | 2/2006 | Becker et al. |
| 2001/0055608 A1 | 12/2001 | Hymes et al. |
| 2002/0132545 A1 | 9/2002 | Lenz |
| 2002/0150720 A1 | 10/2002 | Howard et al. |
| 2002/0156411 A1 | 10/2002 | Ahrens et al. |
| 2002/0172709 A1 | 11/2002 | Nielsen et al. |
| 2002/0197257 A1 | 12/2002 | Meyer-Ingold et al. |
| 2003/0091736 A1 | 5/2003 | Zschaeck |
| 2003/0170314 A1 | 9/2003 | Burrell et al. |
| 2003/0176827 A1 | 9/2003 | Chandra et al. |
| 2003/0185901 A1 | 10/2003 | Burrell et al. |
| 2003/0194444 A1 | 10/2003 | Burrell et al. |
| 2003/0208150 A1 | 11/2003 | Bruder et al. |
| 2004/0002675 A1 | 1/2004 | Nierle et al. |
| 2004/0009202 A1 | 1/2004 | Woller |
| 2004/0010215 A1 | 1/2004 | Gibbins et al. |
| 2004/0030276 A1 | 2/2004 | Flick |
| 2004/0058013 A1 | 3/2004 | Taylor et al. |
| 2004/0086549 A1 | 5/2004 | Nielsen |
| 2004/0091521 A1 | 5/2004 | Radloff et al. |
| 2005/0244484 A1 | 11/2005 | Flick |

FOREIGN PATENT DOCUMENTS

| | | |
|---|---|---|
| EP | 0128338 | 12/1984 |
| EP | 0254413 | 1/1988 |
| EP | 0291587 | 11/1988 |
| EP | 0 344 090 | 11/1989 |
| EP | 0344090 | 11/1989 |
| EP | 0354315 | 2/1990 |
| EP | 0 367 320 | 5/1990 |
| EP | 0392640 | 10/1990 |
| EP | 1 159 972 | 5/2001 |
| GB | 2127389 | 4/1984 |
| GB | 2188135 | 9/1987 |
| WO | WO90/08470 | 8/1990 |
| WO | WO91/11206 | 8/1991 |
| WO | WO92/13491 | 8/1992 |
| WO | WO99/15101 | 4/1999 |
| WO | WO 00/25726 | 5/2000 |
| WO | WO 00/73552 | 12/2000 |
| WO | WO 02/099181 | 12/2002 |
| WO | WO 03/022317 | 3/2003 |
| WO | WO 2004/002384 | 1/2004 |
| WO | WO 2004/037186 | 5/2004 |

OTHER PUBLICATIONS

U.S. Appl. No. 09/613,961, filed Jul. 11, 2000, Flick.
Becker R.O. and Spadaro J.A., *Treatment of Orthopaedic Infections with Electrically Generated Silver Ions*, Journ. of Bone and Joint Surgery, Oct. 1978, vol. 60-A, No. 7, pp. 871-881.
Berger T.J., Spadaro J.A., Bierman, R., Chapin S.E., Becker R.O., *Antifungal Properties of Electrically Generated Metallic Ions.*, Atimicrobial-Agents and Chemotherapy, Nov. 1976, vol. 10, No. 5, pp. 856-860.
Foulds, I.S. and Barker A.T. *Human skin battery potentials and their possible role in wound healing*, British Jorn. of Dermatology, Mar. 1983, 109 pp. 515-522.
Friedenberg Z.B. *Bioelectric Potentials in Bone.* Journ. of Bone and Joint Surgery, Jul. 1966, vol. 48-A, No. 5, pp. 915-923.
Illingworth, C.M and Barker A.T. *Measurement of Electrical Currents Emerging During the Regeneration of Amputated Finger Tips in Children*, Clin. Phys. Physiological Measurements, 1980, vol. 1, No. 1, pp. 87-89.
Jaffe, L.F. and Vanable J.W., Jr. *Electric Fields and Wound Healing*, Clinics in Dermatology, Jul.-Sep. 1984, vol. 2, No. 3, pp. 34-44.
McCaffery M., Pasero C., *Pain: Clinical Manual*, Second Edition, Mosby, pp. 62-65.
Ohnhaus E.E. and Adler R. *Methodological Problems in the Measurement of Pain: A Comparison Between the Verbal Rating Scale and the Visual Analouge Scale*, Pain, 1975, Elsevier/North-Holland, Amsterdam, pp. 379-384.
Pain Assessment and Management: An Organizational Approach, Joint Commission, Chapter Three: Assessment of Persons with Pain, pp. 13-25.
Smee L., *The Effectiveness of Silver Nylon Cloth and Silver Sulfadiazine Cream as Antiseptics*, Piedmont College Senior Thesis, Apr. 1996, USA.
Sriwatanakul K., Kelvie W., Lasagna L., Calimlim, J.F., Weis O.F., Mehta G. *Studies with Different Types of Visual Analog Scales for Measurement of Pain*, Dept. of Pharmacol. Ther., Aug. 1983, pp. 234-239.
Spadaro J.A., Berger T .J., Barranco S.D., Chapin S.E., Becker R.O. *Antibacterial Effects of Silver Electrodes with Weak Direct Current*, Atimicrobial-Agents and Chemotherapy., Nov. 1974, vol. 6, No. 5, pp. 637-642.
Vanable J.W., Jr. *Integumentary Potentials and Wound Healing*, Elec. Fields In Vertebrate Repair, 1989, pp. 171-224.
Westaim Biomedical Commercial Literature, bearing 1988 Copyright notice and product label bearing Acticoat. RTM.
Khanna, A., Sivaraman, R., and Vohora S.B. *Analgesic Activity of Silver Preparations Used in Indian Systems of Medicine*. Indian Journal of Pharmacology, 1997, 29:393-398.

Partial European Search Report for EP 98 94 9403 dated Jul. 2, 2004.
U.S. Appl. No. 09/613,961, filed Jul. 11, 2000, Flick.
U.S. Appl. No. 11/220,566, filed Sep. 6, 2005, Becker et al.
U.S. Appl. No. 11/255,492, filed Oct. 21, 2005, Flick et al.
Becker et al., "Clinical Exp. With Low Intensity Direct Current Stimulation of Bone Growth," *Clin. Orthop. & Rel. Res.*, (1977) vol. 124, pp. 75-83.
Becker et al., "Electrochemical Mechanisms and the Control of Biological Growth Processes," *Modern Aspects of Electrochemistry*, (1971) No. 10, pp. 289-338.
Becker et al., "Experience with Low-Current Silver Electrode Treatment of Nonunion," *Electrical Prop. Bone & Cartilage* (ed. C.T. Brighton, et al.), (1979).
Berger et al., "Electrically Generated Silver Ions: Quantitative Effects on Bacterial & Mammalian Cells," *Antimicrob. Agents & Chemother*, (1976) vol. 9, pp. 357-358.
Hill et al., "Inhibitory and Cidel Antimicrobial Actions of Electrically Generated Silver Ions," *J. Oral & Maxillofac. Surg.*, (1987) vol. 45, pp. 779-784.
Marino et al., "Electrochemical Properties of Silver-Nylon Fabrics," *Electrochemical Science and Technology*, (1985) vol. 132, No. 1, pp. 68-72.
Spadaro et al., "Experience with Anodic Silver in the Treatment of Osteomyelitis," 25$^{th}$ Ann. ORS Mtg., (Feb. 20-22, 1979).
Spadaro et al., "Some Specific Cellular Effects of Electrically Injected Silver & Gold Ions," *Bioelectrochem. & Bioenergetics*, (1976) vol. 3, pp. 49-57.
Urist et al., "Bone Morphogenesis in Implants of Insoluble Bone Gelatin," *Proc. Nat. Acad. Sci. USA*, (1973) vol. 70, No. 12, Part I, pp. 3511-3515.

Patricia C. MacKeen, et al., *Silver-Coated Nylon Fiber as an Antibacterial Agent*, Antimicrobial Agents and Chemotherapy, p. 93-99 (American Society for Microbiology—Jan. 1987).
Edwin A. Deitch, et al., *Silver-Nylon: A New Antimicrobial Agent*, Antimicrobial Agents and Chemotherapy, pp. 356-359 (American Society for Microbiology—Mar. 1983).
Perry J. Riggle, et al., *Role of a Candida albicans PI-Type ATPase in Resistance to Copper and Silver Ion Toxicity*, Journal of Bacteriology, pp. 4899-4905 (American Society for Microbiology—Sep. 2000).
Complaint—Noble Fiber Technologies, LLC v. Argentum Medical, LLC, Civil Action No. 3:05-CV-01855-ARC, filed Sep. 13, 2005.
Deitch, et al., "Silver-impregnated nylon cloth dressing", *Burns*, 13 (5):423 (1987) (Abstract).
Marino, et al., "Electric silver antisepsis", *IEEE Trans. Biomed. Eng.*, 32(5):336-7 (1985).
Marino, et al., "Electrical augmentation of the antimicrobial activity of silver-nylon fabrics", *J. Biol. Phys.*, 12(4):93-8 (1984).
McManus, "The burn wound: effect of silver nylon dressing and DC", *Pathophysiology*, 121 (1994) (Abstract).
Schierholz, et al., "Efficacy of silver-coated medical devices", *J. Hosp. Infect.*, 40(4):257-62 (1998).
Amended Complaint—Noble Fiber Technologies, LLC v. Argentum Medical, LLC et al., Civil Action No. 3:05-cv-01855-ARC filed Oct. 21, 2005.
US 5,872,068, 02/1999, Cartwright et al. (withdrawn)

* cited by examiner

MULTILAYER CONDUCTIVE APPLIANCE HAVING WOUND HEALING AND ANALGESIC PROPERTIES

CROSS-REFERENCE TO RELATED APPLICATION

This application is a Continuation of U.S. application Ser. No. 09/531,245 filed on Mar. 21, 2000 now U.S. Pat. No. 6,861,570, which is a Continuation of prior International Application Serial No. PCT/US98/19689 filed on Sep. 22, 1998, which is a continuation of U.S. application Ser. No. 08/935,026 filed on Sep. 22, 1997, now U.S. Pat. No. 6,087,549.

TECHNICAL FIELD OF THE INVENTION

The present invention relates to wound dressings and medical devices for restoring the premorbid electro-biological activity of tissue systems that are altered by pathological conditions in the animal and human body. More particularly, it relates to metalized dressings and medical devices that enhance tissue healing and reduce the perception of pain by influencing in a passive (non energy requiring) manner the electrical parameters of the injured tissue and that may also exhibit antibacterial and antifungal efficacy.

BACKGROUND ART

Wound treatment has become a more highly developed area of scientific and commercial investigation as new research has revealed the workings of the healing process. More rapid healing of a wound reduces long term healthcare costs and improves patient recovery, including regaining of sensation, function and aesthetics.

Healing, like all other biological processes, is a cellular process. The occurrence of an injury immediately triggers the onset of this process, which continues until the injury is healed. Although its exact mode of action is not yet understood, it is clear that a feedback mechanism monitors the extent of tissue damage and adjusts cellular activity in the injured area to produce the exact amount of healing needed.

As used herein, the terms 'wound' and "injury" refer to tissue damage or loss of any kind, including but not limited to, cuts, incisions (including surgical incisions), abrasions, lacerations, fractures, contusions, burns, amputations and the like.

Healing in general is known to be related to the degree of the injury, and the electrical potential difference between the site and surrounding intact tissue. In particular, regeneration in amphibians such as salamanders and fracture healing in mammals are associated with complex changes in the local DC (direct current) electric field. The electric field gradually returns to normal, pre-injury levels as the injury heals. Conversely, failure of the normal healing process, as in fracture nonunions, is associated with the absence of appropriate electrical signals at the site of the injury.

More particularly, and by way of example, healthy human skin exhibits an electrical potential across the epithelium, i.e., the transepithelial potential (TEP or epidermal battery). The TEP is generated by an active ionic transfer system. Sodium ions enter the outer cells of the epithelium via specific channels in the outer membrane of these cells and migrate along a steep electrochemical gradient. Through a series of electrogenic pumps that actively pump sodium ions and tight gap junctions between epithelial cells that do not allow the reverse passage of the sodium ions, the epidermal battery is generated. This results in a transport of sodium ions from the water bathing the epithelium to the internal body fluids of the animal, and the generation of a potential of the order of 10 mV to 70 mV across the epithelium.

While the general topic of wound healing has an extensive and broad literature base with excellent review papers written by Eaglstein 1984, and Eckersley and Dudley 1988, published research on the role of generated electrical potentials in the healing process has been limited.

Notwithstanding, the existence of wound currents has been recognized for more than 200 years. In early experiments, about 1 µA of current was found to leave a wound in human skin immersed in saline (Barker 1982, Jaffe 1984). In 1980, lllingworth and Barker measured currents with densities of from 10–30 $\mu A/cm^2$ leaving the stump surface of children's fingers whose tips had been accidently amputated. This outflowing of current has also been called the "Current of Injury". It is generally recognized that the electromotive force (EMF) driving currents from wounds made in skin is a direct result of disruption of the transepithelial potential (TEP). It is generally believed that ionic currents primarily generated by the epithelium's electrogenic sodium transport mechanism are responsible for the TEPlkk (epidermal battery). Founds and Barker (1983) recorded the TEP of human skin with values ranging from about minus 10 mV to almost minus 60 mV depending on the region measured. Barker (1982) reported that interruption of the sodium transport system by a blocking agent called amiloride, resulted in a reduced TEP. When amiloride is added to areas of wounding such as a laceration, the TEP is reduced to about one half its original value and the healing process was significantly slowed.

Borgens (1982) has reported that trauma or tissue damage disrupts the normal electrical pattern of the cell, tissue, or organism. It is believed that the altered electrical profile serves as a signal for or a causative agent in the repair or regenerative process.

Barker (1982) recognized that when a wound is made in the skin, an electric leak is produced that short-circuits the TEP (epidermal battery) allowing the voltage to reverse at the wound surface. With the disruption of the epithelium's electrogenic sodium transport mechanism within the wound, the TEP on the surface of the wound is significantly altered in the reverse direction. As one progresses laterally from the wound surface to normal tissue surrounding the wound, the potential across the skin is found to increase, until a point is reached at which the potential across the skin is the full value normally found in unwounded skin. Thus a lateral voltage gradient is generated in the proximity of the wound margin as one transitions from wounded tissue to normal tissue. Jaffe and Vanable (1984) have reported the lateral voltage gradient in experimental animals could be as high as 140 mV/mm. It has also been reported that within 24 hours after a wound, the epidermally generated lateral voltage drops by 95%. Therefore, it is recognized that there is a lateral voltage gradient or "lateral potential" in the epidermis close to the margin of a wound. The greatest epidermally generated lateral voltage is found in the region of highest tissue resistance. In the amphibian, the locus of the major lateral potential is at the high resistance space between the epidermis and the dermis; whereas, in the mammal, the locus of the major lateral potential is at the space between the living and the dead cornified layers of epithelium.

The role that endogenous electric fields play in bone physiology and the repair process is well documented in the medical literature. Friedenberg and Brighton first reported in 1966 that a peak of electronegativity occurred at a fracture site, along with a general electronegativity of the entire bone, when referred to the proximal epiphysis. They also noted peaks of electronegativity were measured on the skin over tibial fractures in both rabbits and humans.

There have been numerous studies conducted on the wound healing of amphibians due to the phenomenon of tissue regeneration by amphibians and because the rate of wound healing is significantly greater in amphibians than in mammals.

Winter (1964) reported that wound healing in mammalian skin occurs over days or even weeks, with epithelial cell migration rates ranging from 7 (dry wound) to 20 (wet wound) micrometers/hour. Amphibian skin wounds heal within hours, with epithelial cell migration rates ranging from 60 to more than 600 micrometers/hr. The difference in the rates of healing of mammalian skin and amphibian may be partially explained by environmental factors. More specifically, the aqueous environment of an amphibian bathes the outer surface of the epithelium and the dead cornified layer is thin and moist. As a result, the cornified layer is not a significant barrier to the movement of sodium ions into the epidermal cells. In contrast, the dead, cornified layer of mammalian skin is thick and dry, representing a significant barrier to the movement of sodium ions into the epidermal cells. It is generally recognized that dry wounds (as in mammals) heal more slowly than wounds that are kept moist by occlusive dressings. Keeping the epidermis surrounding a wound and the wound itself moist stimulates the wound to close.

In summary, it has been recognized that keeping wounds moist may simulate an environment like that which exists in amphibian healing and accelerating the mammalian healing process. U.S. Pat. No. 5,512,041 of Bogart teaches a wound dressing that promotes moist wound healing comprising a backing sheet coated with a pressure sensitive adhesive, an absorbent pad and a net extending across the pad and attached to the adhesive.

Besides the effect of moisture on wound healing, microbial growth at the site of injury has a great effect on healing time, with low bacterial counts (less than $10^2$ to $10^3$) promoting healing. While there are scores of antibacterial and antifungal agents, the efficacy of silver is of particular interest herein. The antimicrobial and antifungal properties of silver and silver compounds are well known. Topical preparations that contain silver or silver compounds-silver nitrate solution, silver sulfadiazine cream, colloidal silver compositions, silver-protein compounds such as Argyrol, and so forth, have been and some are widely used in medicine. The useful effects of these compositions are due to the small amounts of free silver ions produced by dissociation of the silver moiety from the compound to form ionic silver.

The effectiveness of silver as an antimicrobial agent is at least partly determined by the delivery system. Most silver compounds that dissociate readily (silver nitrate) and produce large numbers of free silver ions are highly toxic to mammalian (including human) tissues. Less-toxic compounds, including silver sulfadiazine cream (widely used in the treatment of burns) do not dissociate readily and therefore do not release large numbers of silver ions. These compounds must be re-applied frequently to maintain their clinical efficacy.

Silver and other metals have been reported to be used in wound dressings and materials therefor. Antimicrobial activity may be achieved by pure metals, metal salts, metal organic compounds or combinations of metals to create a galvanic cell reaction. Fabo (U.S. Pat. No. 5,340,363) discloses a dressing that includes an outer absorbent layer and an inner porous, hydrophobic layer knitted of elastic threads and encapsulated by a soft, hydrophobic silicone or polyurethane gel. The gel can be used as a carrier for antibacterial agents such as zinc, pain-relieving substances, and agents that stimulate wound repair. Klippel et al. (U.S. Pat. No. 3,830,908) use micronized allantoin as a carrier for a bactericidal or bacteriostatic ingredient (such as silver citro allantoinate) that is dispersed on the surface of a plastic air splint or other bandaging product. This material depends on the separation of the molecular moieties to provide the antibacterial action.

McKnight et al. (U.S. Pat. No. 3,800,792) disclose a surgical dressing having a layer of tanned, reconstituted collagen foam film laminated to a thick, continuous layer of an inert polymer. The collagen layer contains finely-divided silver metal added by soaking the collagen film in Tollen's reagent. Stowasser (U.S. Pat. No. 2,934,066) makes a dressing of absorbent metal-coated fibers, such as a carding fleece coated with aluminum and backed by compressed cellulose, and polyamide fibers coated with vacuum-deposited silver.

U.S. Pat. No. 5,782,788 of Widemire teaches that a layer of silver foil affixed to a gauze pad inhibits the growth of bacteria, viruses, and fungi by providing a source of silver ions that are driven off the foil by the negative DC field of the body.

U.S. Pat. Nos. 5,454,886, 5,681,575, and 5,770,255 to Burrell teaches a vapour deposition technique for the purpose of a sustained release of metal ions sufficient to produce an anti-microbial effect. U.S. Pat. No. 5,695,857 to Burrell teaches an active antimicrobial surface that comprises a film consisting of at least an antimicrobial element and another electrochemically nobler element and forms a multilayer galvanic cell for releasing the antimicrobial element at the surface.

Dressings for provision of electrical stimulation are also known. For example, Jones (U.S. Pat. No. 4,911,688) covers a wound with a clear cover that serves as a hollow chamber for holding a fluid such as saline in contact with a wound. When connected to a voltage source, a metal anode and a return electrode create free ions and an electrical field to enhance healing and tissue regeneration. Juhasz (U.S. Pat. No. 4,817,594) discloses a multi-layer dressing for covering discharging, malodorous wounds. The dressing includes an open mesh layer of an electrically-conductive material such as silver and a layer of charcoal fabric. Seiderman (U.S. Pat. No. 4,767,401) teaches a bandage-like device used for iontophoretic administration of medicaments, including silver-protein colloids. The device includes a metal foil electrode (preferably aluminum), and makes use of the slight inherent negative electric charge proximate a wound site to generate a small electric field at the site.

Matson (U.S. Pat. No. 4,728,323) coats a substrate (nylon fabric, polymeric film, fiberglass, gauze or polyurethane foam) with a film of a silver salt, e.g., silver chloride or silver sulfate deposited by vapor or sputter coating techniques to provide an antimicrobial effect. Alternatively, fibers can be coated and then woven or knitted into a fabric. Other silver salts referred to in this patent are silver bromide, silver fluoride, silver chloride, silver nitrate, silver sulfate, silver alkylcarboxylate, silver sulphadiazine, and silver arylsulfonate. In the dry crystalline form these salts deposited as thin films are diaelectric materials with extremely poor conductivity. When the crystalline salts are immersed in physiological solutions they continue to exhibit their dielectric characteristics. Konikoff (U.S. Pat. No. 4,142,521) shows a bandage or surgical sponge material incorporating one or more electret elements, each electret providing a small electrostatic field to the area of the wound.

Spadaro (1974) and Becker (1976) reported electrically-generated silver ions, could can penetrate deeply into the tissues, were noted to be effective even against antibiotic-resistant strains of bacteria, fungi, etc., inhibiting growth in vivo and in vitro at current densities as low as 10 $\mu A/mm^2$ and silver ion concentrations as low as 0.5 mg/ml. U.S. Pat. No. 4,528,265 of Becker discloses processes and products that involve subjecting mammalian cells to the influence of electrically-generated silver ions. Anodic silver causes cells such as mammalian fibroblasts to assume a simpler, relatively unspecialized form and to resemble dedifferentiated or embryonic cell types. An iontophoretic system for promoting tissue healing processes and inducing regeneration is described in Becker et al., U.S. patent application Ser. No. 08/623,046, filed Mar. 28, 1996. The system is implemented by placing a flexible, silver-containing anode in contact with the wound, placing a cathode or intact skin near the anode, and applying a wound-specific DC voltage between the anode and the cathode. Electrically-generated silver ions from the anode penetrate into the adjacent tissues and undergo a sequence of reactions leading to formation of a silver-collagen complex. This complex acts as a biological inducer to cause the formation in vivo of an adequate blastema to support regeneration. The above systems have limitations in that either an electrolyte or an external voltage source is required.

Seiderman U.S. Pat. No. 4,034,750 teaches that an electrochemically active ostonic collagen paste capable of generating a galvanic current has the property of electrochemically-linking collagen fibrils to form an adherent skin-like protective membrane. Seiderman notes that when a 10% isotonic collagen paste is applied locally over a wound that an electric field is established between the collagen paste dispersion and the animal body; the paste will exhibit an overall positive charge while the areas surrounding the wound site will exhibit an effective negative electrical potential. It is generally recognized by those skilled in the art that mammalian wounds without treatment or 10% isotonic collagen paste are more positive than the surrounding tissue that will exhibit an effective negative electrical potential.

Regardless of whether silver is provided in the form of silver ions or as a topical composition (silver nitrate solution, silver sulfadiazine cream, or the like), its beneficial effects are manifested primarily at the treated surface and immediately adjacent tissues, and are limited by the achievable tissue concentration of silver ions. Despite the availability of numerous techniques for the delivery of silver and silver compounds in vitro and in vivo, there remains a need for a delivery system that is capable of supplying clinically useful concentrations of silver ions to a treatment site without the need for adjuvant electrical stimulation.

In addition to the foregoing therapeutic strategies, metals have been used to achieve diverse beneficial effects.

U.S. Pat. No. 2,577,945 of Atherton teaches a metallic film for the purpose of providing a heat-reflective surface, touching the body or raised off the body. The heat reflective surface would conserve the heat from the wound and thereby assist with wound healing.

U.S. Pat. No. 3,326,213 of Gallaher teaches the application of an electrostatically charged gold leaf film from 0.0003 to 0.1 mil thick to treat damaged mammalian tissue and arrest hemorrhaging vasculature. The electrostatic charge allows the gold leaf to cling to the body tissue.

U.S. Pat. No. 3,420,233 of Kanof teaches application of gold leaf to stimulate epithelialization of an avascular ulcer. An electrostatic differential between the gold leaf and the ulcer is achieved by apply ethyl alcohol to the ulcer.

U.S. Pat. No. 4,297,995 of Golub teaches a metal foil or a metal foil-polyester laminate forming a base plate provides a suitable barrier material for a bandage that can dispense medications.

U.S. Pat. No. 5,374,283 of Flick teaches an electrical apparatus for the treatment of body pain and edema by delivering an electrical signal/voltage.

U.S. Pat. No. 4,619,252 of Ibboott teaches a therapeutic method and therapeutic means for applying a voltage to the human body by a sheetlike battery utilizing a negative electrode composed of a metal foil such as aluminum or zinc.

In reviewing prior art, metal coatings on wound dressings have been used for: (1 thermal activity; (2) for arresting hemorrhaging vasculature; (3) for stimulating wound healing; (4) for a barrier material; (5) for delivery of electrical signals as in the form of an electrode (6) for part of a battery to apply voltage to the human body (7) for antimicrobial activity and (8) for cell modification. The prior art does not teach altering a wound's electrical parameters with a passive, highly conductive element.

The prior art does not address the restoration of a homeostatic electromagnetic field environment for wounded tissue nor the alteration of wound currents that accelerate healing. Accordingly, it is an object of the present invention to provide wound dressings and apparatus which can promote healing, stimulate cell growth, and alleviate pain through electrically conductive elements.

DISCLOSURE OF THE INVENTION

A dressing for promoting healing and pain relief of the body of a living organism having a pathologic condition has at least one layer of conductive material with a resistance no greater than 1000 106 /cm$^2$. When placed proximate a portion of the body of the living organism suffering from the pathologic condition, the dressing alters the electrodynamic processes occurring in conjunction with the pathologic condition to promote healing and pain relief. When used as a wound dressing, the conductive material is placed in contact with healthy tissue around the periphery of the wound and with the wound. In an exemplary embodiment, the conductive material is a multi-ply nylon fabric coated with silver and with the plies in electrical continuity. Alternative embodiments may include other layers such as an absorbent layer, a semi-permeable layer and additional layers of conductor material. Multilaminate embodiments of the present invention exhibit conductive material concentration gradients and, when sequential conductor layers are insulated by intervening layers, a capacitive effect.

BRIEF DESCRIPTION OF THE DRAWINGS

The invention is illustrated in the drawings in which like reference characters designate the same or similar parts throughout the figures of which:

FIG. 9 shows the data using *P.aeruginosa* depicted in FIG. 16.

FIG. 10 shows the data using *E.coli* depicted in FIG. 14.

FIG. 11 shows the data using *E.faecalis* depicted in FIG. 15

FIG. 12 shows the data using *S.aureus* depicted in FIG. 13.

BEST MODE FOR CARRYING OUT THE INVENTION

The present invention encompasses a wound dressing and/or appliance having a highly electrically conductive layer. The highly conductive layer in and of itself has inventive aspects in the identification of its functionality, its formation and use. The highly conductive layer may be used in combination with other dressing layers. In describing the present invention, the multilaminate composite shall be described first followed by a description of the form and function of the highly conductive layer.

Figure 1:
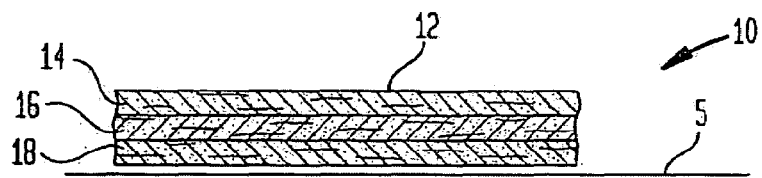
FIG. 1 is a schematic cross-sectional view of the laminate structure of a first embodiment of the present invention.

Referring to FIG. 1, a first embodiment of the present invention includes a laminate structure 10 composed of at least two layers that is applied to a body surface such as the skin 5. In the embodiment shown, three layers of material 14, 16 and 18, are utilized. Any number of layers could be utilized depending on the composition, thickness, denier, fiber density and other characteristics of the material. There are also practical limits on the number of layers of material usable, such as cost or material bulk which begin to outweigh the incremental benefits of an additional layer.

Each layer 14, 16 and 18 is a flexible material preferably composed of a mixture of silvered fibers and nonmetalized fibers. The silver is preferably of high purity, preferably from about 99.0% to about 99.9%, although lower purity levels can function in the present invention. High purity reduces the likelihood that contaminants or undesirable ions may contact or penetrate the wound or skin. The base fiber is preferably nylon, although other polymers or materials can be used with the present invention. The most important qualities of the base fiber are that it must be flexible and it must be capable of being coated with a metal or metals. The base fiber may be the same as the non-metallized fibers.

Each of the base fibers is completely coated with metallic silver by an autocatalytic electroless plating process. The thickness of the uniform coating varies from 0.2 micrometers to 1.0 micrometer. The thickness of coating is reported in the percentage of weight of silver plated to the weight of the fabric without silver plating. The amount of coating may vary from about 5% to about 40% by weight, more preferably about 15% by weight.

The silver fibers are commercially available from Omnishied, Inc., Clarks Summit, Pa., Swift Metalizing Corp., Hartford, Conn., and Sauquoit Industries, Inc., Scranton, Pa. The denier of the silver fibers is in the range of from about 1 denier to about 120 denier, more preferably of from about 3 denier to about 80 denier, and still more preferably about 3 denier to 24 denier.

The base fiber is preferably a flexible material, such as, but not limited to, acetate, flax, glass, modacrylic, olefin polyester and polyethylenes, rubber, saran, spandex, vinyl, vinyon, cotton, wool, silk or other natural fiber, rayon, nylon, glasswool, acrylic, synthetic polymers, such as polyolefins sold under the trademarks DELNET, and STRING-NET, other synthetic materials, blends or multicomponent fibers, either woven or nonwoven. The material chosen should be flexible, nonconductive, preferably biologically inert, flexible nonconductive and also preferably nonimmunogenic. Since some individuals may have a topical hypersensitivity to certain fiber materials, the base fiber is preferably nonallergenic or hypoallergenic. Preferred base fibers are nylon, rayon, glass, silk, polyolefin or cotton. It is to be understood that other fiber materials can be used to achieve the objects of the present invention.

Figure 1A:
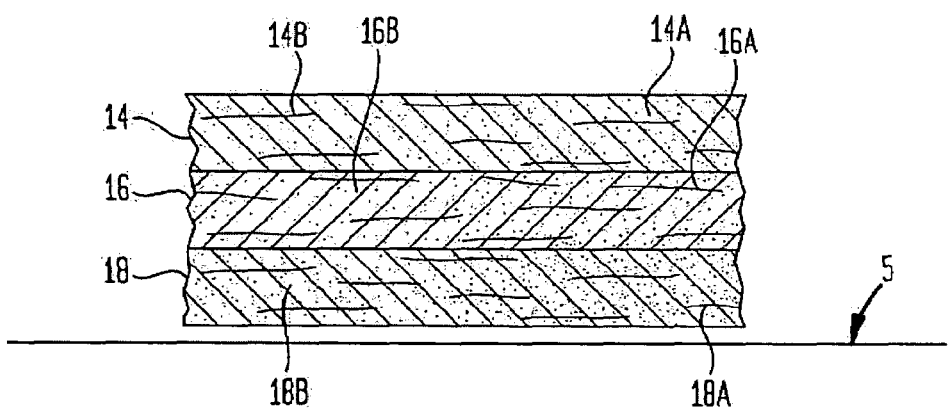
FIG. 1A is a schematic cross-sectional view of a second embodiment of the present invention showing a gradient of silver fiber concentration in the material, as depicted by a varying stippling density.

In a first embodiment, the silver fibers and nonmetalized fibers are generally equally distributed throughout each layer 14, 16, 18 of the material. For example, the silvered fibers may be mixed with the nonmetalized fibers by air to create a random, generally uniform mixture of fibers. Alternatively, it is contemplated as being within the scope of the present invention to have areas of different fiber distribution for certain applications. FIG. 1A shows an alternative embodiment wherein one portion 14A, 16A or 18A of layers 14, 16, 18 has a higher average concentration or density of metalized fibers than a second portion 14B, 16B or 18B. Gradient concentration of mixed fibers can be made according to processes known to those of ordinary skill in the art. An application of a controlled fiber distribution is for a body cavity area dressing, such as, but not limited to, a vaginal or rectal area dressing. The mucosal tissue of such body cavities as the vagina and rectum require much lower percentage concentrations of silver fibers than epithelial tissue such as skin.

The ratio of silvered fibers to nonmetalized fibers is an important aspect of the present invention. In a given layer, the ratio of silver fibers to nonmetalized fibers can be from about 1:100 to about 1:1 more preferably from about 1:50 to about 1:2, and still more preferably from about 1:20 to about 1:4. Where the layers are 100% silver nylon, the ratio would be about 1:0. The layers of material are arranged so that the layer which will be in contact with the body, e.g., a wound site or vaginal wall, has the highest ratio, with a layer next removed from the wound site having a lower ratio, and so forth. Thus, there is a decreasing concentration gradient of silvered fibers in subsequent layers 14,16,18 further from the wound site.

In addition to a decreasing concentration gradient, the thickness of the layers preferably, although not mandatorily, increases as the distance from the body, e.g, skin, increases; i.e., the thickness of the layer 14 next to the skin 5 is preferably less than the thickness of the layer 16 and 18 farther from the skin.

The layers 14, 16 and 18 can be laminated by sonic welding, adhesives, heated calendar rolls, needle punching, hydraulic needling or other fiber layer laminating or joining processes known to those of ordinary skill in the art. In a needle punching process, the layers are superimposed and passed through a pair of niprolls, one of the niprolls having series of spaced apart pins, needles or other protrusions extending radially therefrom, and the other niproll being smooth. The pins enter the fabric layers 14, 16, 18 and push fibers from one layer into another layer, creating a physical bonding between the layers. After passing through the niproll assembly, the laminate structure can be wound up on a take up roll or further processed.

The laminate structure 10 is semipermeable to most substances. A layer may be added that would function as a semiocclusive membrane permitting gas exchange but retarding the rate of water loss. Moisture retention of the structure 10 keeps the wound site moist to promote healing. Preferably, the structure 10 has a permeability to water vapor from about 500 grams/square meter/24 hours to about 3000 grams/square meter/24 hours.

Figure 2:
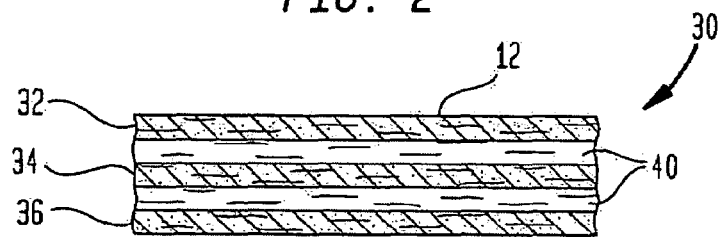
FIG. 2 is a schematic cross-sectional view of the laminate structure of a third embodiment of the present invention.

In an alternative embodiment, shown in FIG. 2, a laminate structure 20 is comprised of layers 24, 26 and 28 of the mixed silvered fiber/nonsilvered fiber material like that of layers 14, 16, 18 of FIG. 1. Between each layer 24, 26, 28 is a layer of a nonconducting flexible material 22 that can be any flexible, porous material that is immunogenically inert and semipermeable. Such materials include, but are not limited to acetate, flax, glass, modacrylic, olefin polyester and polyethylenes, rubber, saran, spandex, vinyl, vinyon, cotton, wool, silk or other natural fiber, rayon, nylon, glasswool, acrylic, synthetic polymers, such as, polyolefins sold under the trademarks DELNET, and STRINGNET, other synthetic materials, blends or multicomponent fibers, either woven or nonwoven. A preferred material is DelNet®, a high density polyethylene blend available from Applied Extrusion Technologies, Inc., Middletown, Del. The use of the alternating layers 24, 26, 28 of silver-containing material and nonsilvered layers 22 creates a capacitor-like laminate, as will be described in greater detail hereinbelow.

The present invention as described above is primarily usable as a dressing to promote wound healing. The present invention also is usable as an antibacterial and antifungal. Surprisingly, the present invention also appears to have analgesic properties. The anticipated mode of operation of the present invention shall be described more fully below. Prior to such description, additional examples of the present invention shall be described.

Figure 3:
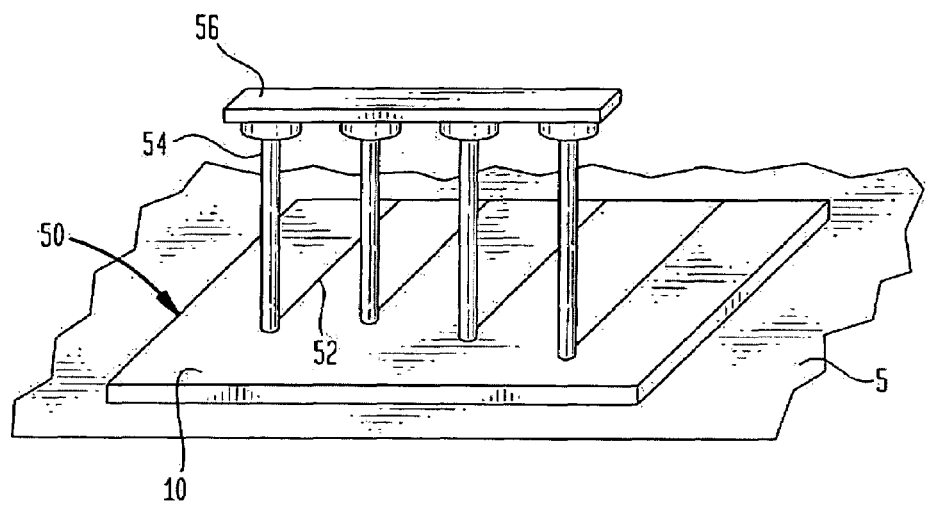
FIG. 3 is a schematic perspective view of a dressing according to a fourth embodiment of the present invention for use around an external fixature pin structure.

The laminate structure 10 or 20 of the present invention can be formed into any of a number of possible shapes, patterns or geometrics, depending on the application and topography of the wound or application site. Several examples are shown in FIGS. 3–8. FIG. 3 shows a dressing 30 with a composition like that of structures 10 or 20 having a plurality of slits 32 for accommodating a set of fixature pins 34 that extend through the skin 5 and which are joined by cross bar 36. The dressing 30 is appropriate for use in maintaining an antimicrobial environment, reducing pain and inducing healing.

Figure 4A:
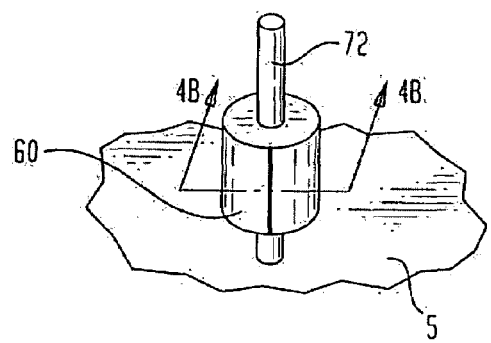
FIG. 4 is a schematic perspective view of a dressing according to a fifth embodiment of the present invention for use around a pin extending from the skin.
Figure 4B:
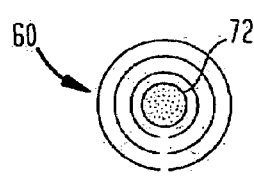
Figure 4C:
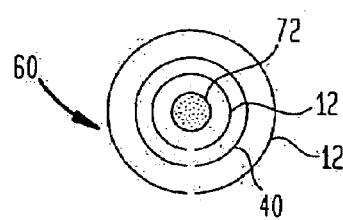

FIG. 4A shows a sleeve 40 made from laminate material 10 or 20 rolled into a cylinder for placement over a pin 42, such as would be used for external orthopaedic fixation devices.

Figure 5:
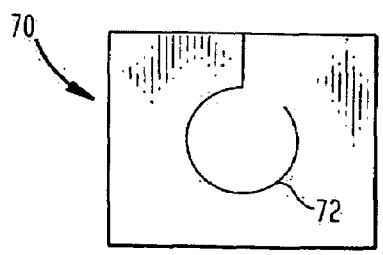
FIG. 5 is a schematic plan view of a dressing according to a sixth embodiment of the present invention for use at an ostomy site.

FIG. 5 shows a dressing 50 constructed of material 10 or 20 with a circular slit 52, usable as a dressing for an ostomy surgical site, or in conjunction with a feeding tube (not shown).

Figure 6:
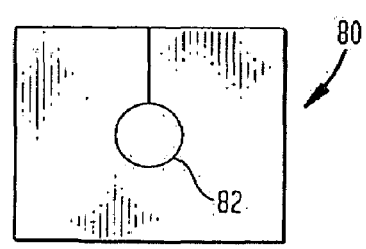
FIG. 6 is a schematic plan view of a dressing according to a seventh embodiment of the present invention for use at a tracheostomy site.

FIG. 6 shows a dressing 60 formed from material 10 or 20 with a circular opening 62, usable as a dressing for a tracheostomy surgical site.

Figure 7A:
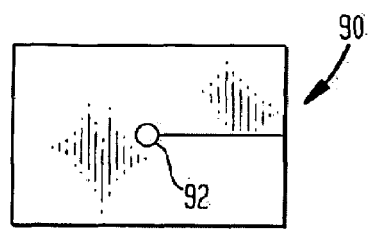
FIG. 7A is a schematic plan view of a dressing according to an eighth embodiment of the present invention for use at an i.v. catheter site.
Figure 7B:
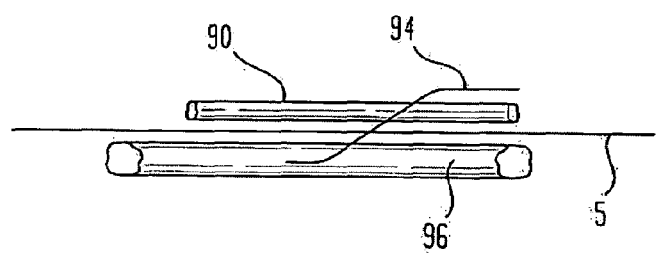
FIG. 7B is a schematic side view of a dressing according to FIG. 7A in situ.

FIG. 7A shows a dressing 70, similar to dressing 60, but with a smaller opening or a cross slit forming an "x" 72, usable in conjunction with an i.v. catheter. FIG. 7B shows a catheter 74 inserted through the skin 5 to vein 76. The dressing 70 is placed around the catheter 74.

Figure 8:
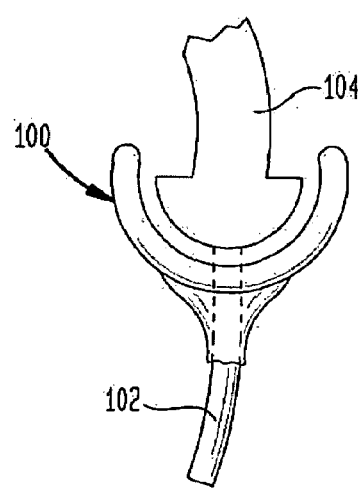
FIG. 8 is a schematic view of a dressing according to a ninth embodiment of the present invention for use with a urinary catheter.
Figure 9:
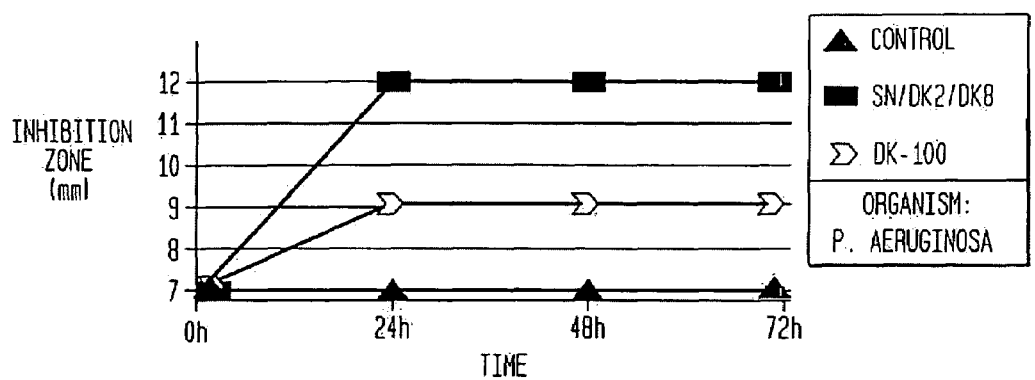
FIGS. 9–12 are graphs of the experimental data pertaining to the microbial inhibition zone achieved in cultures of several organisms by various materials, including a material in accordance with the present invention.
Figure 10:
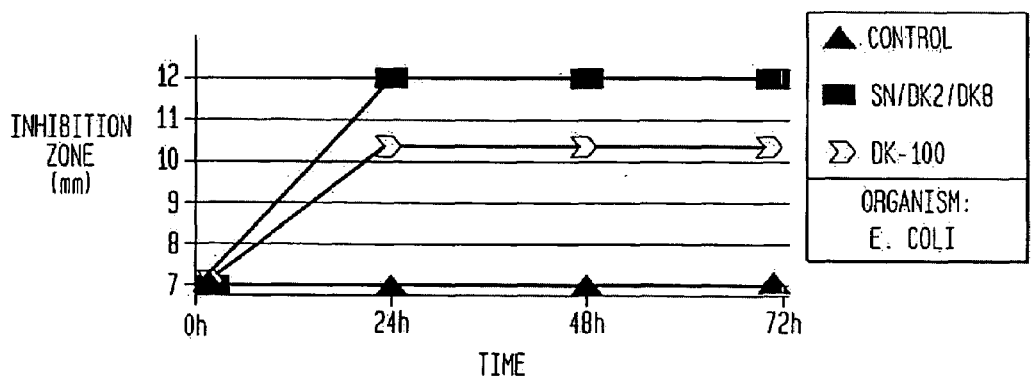
Figure 11:
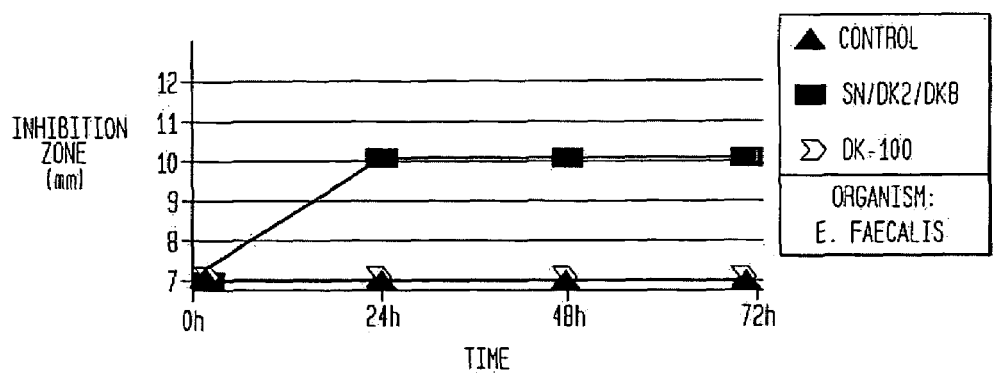
Figure 12:
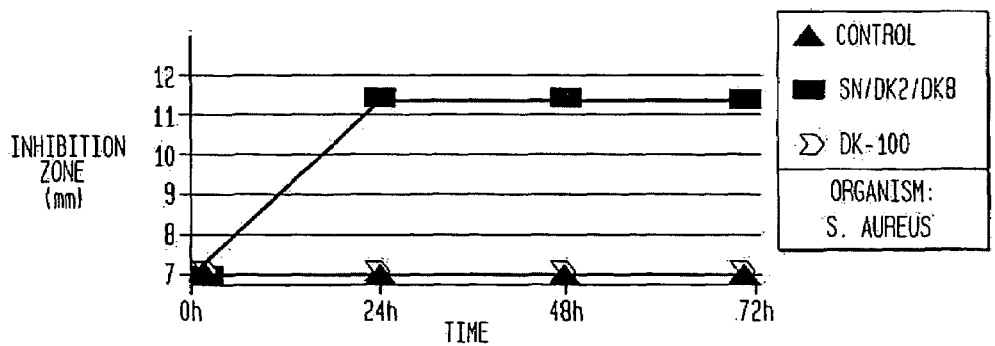
Figure 13:
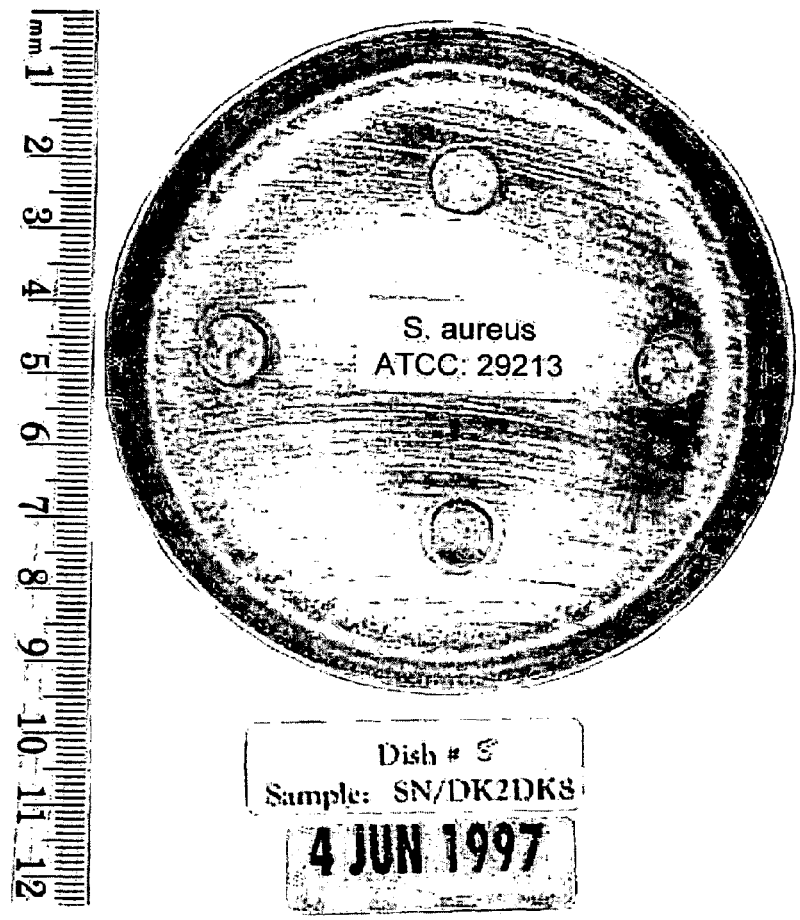
FIGS. 13–16 are photographs of different Petri dishes containing the labeled bacteria, showing the zones of inhibition that form the basis for FIGS. 9–12.
Figure 14:
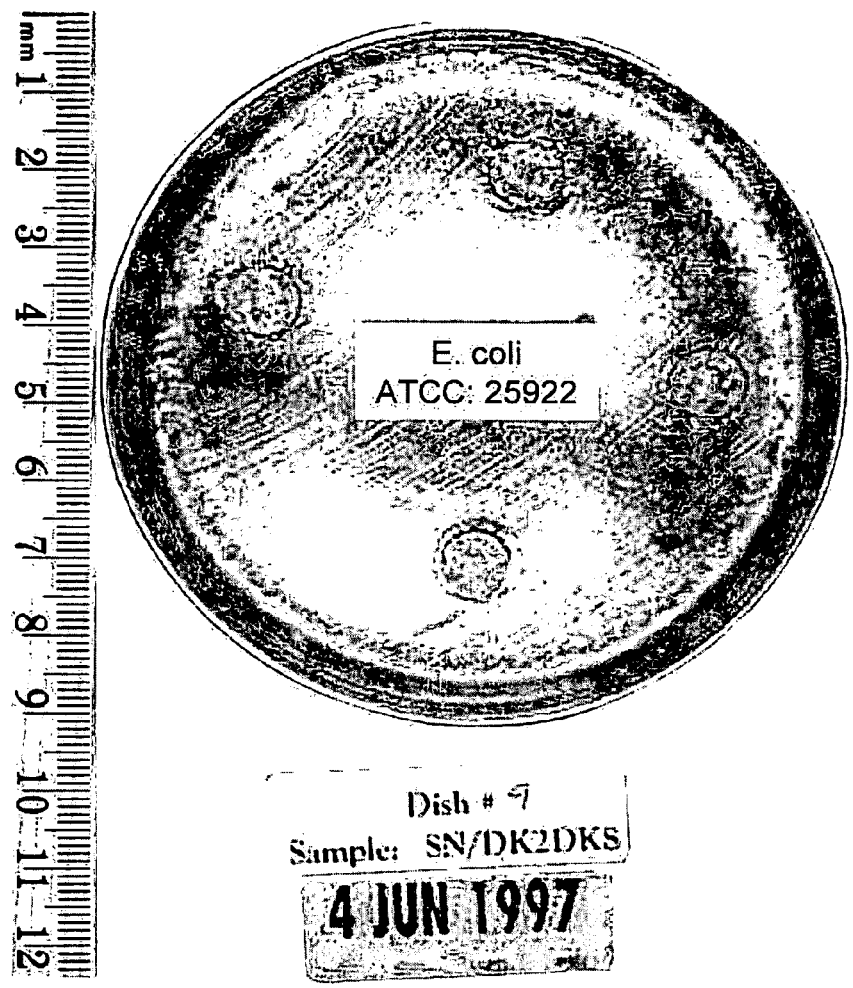
Figure 15:
Figure 16:
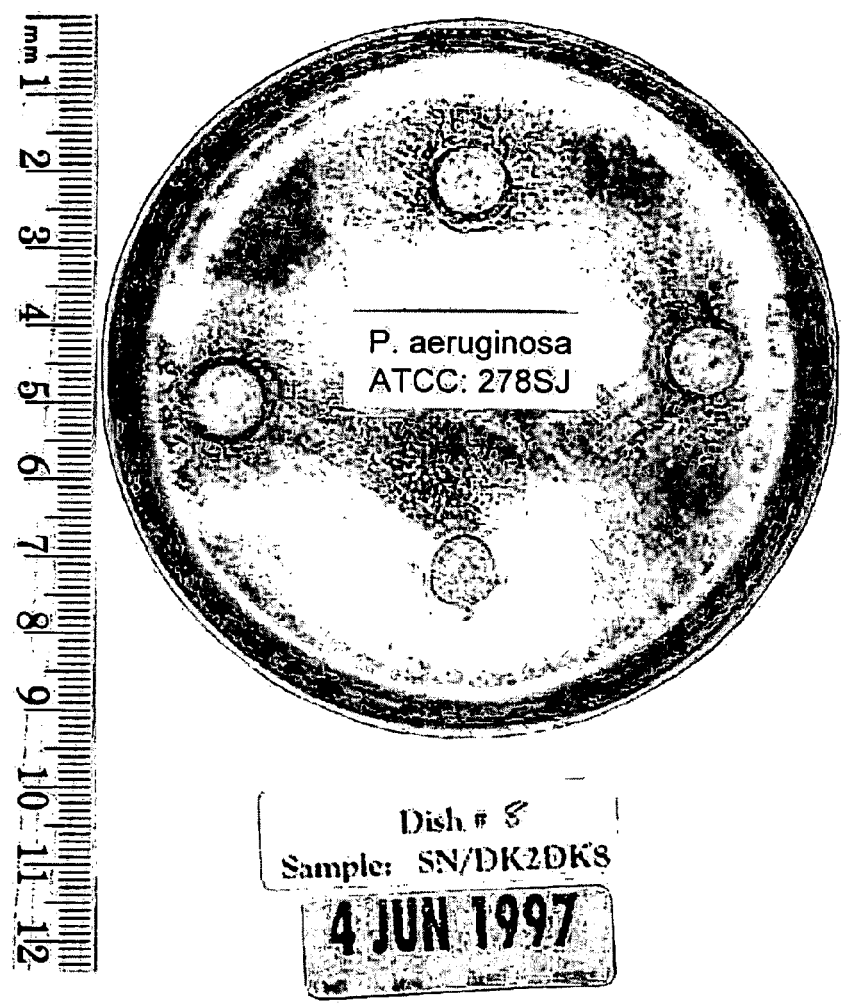
Figure 17:
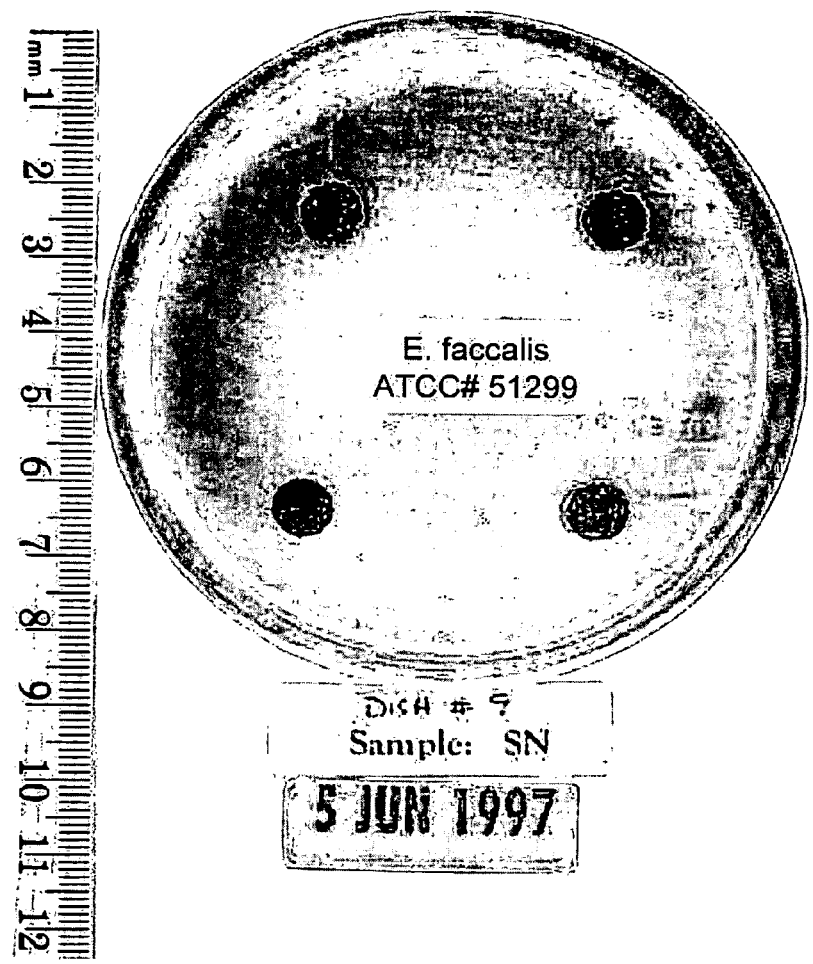
FIGS. 17 and 18 are antibiotic resistant bacteria showing excellent zones of inhibition.
Figure 18:
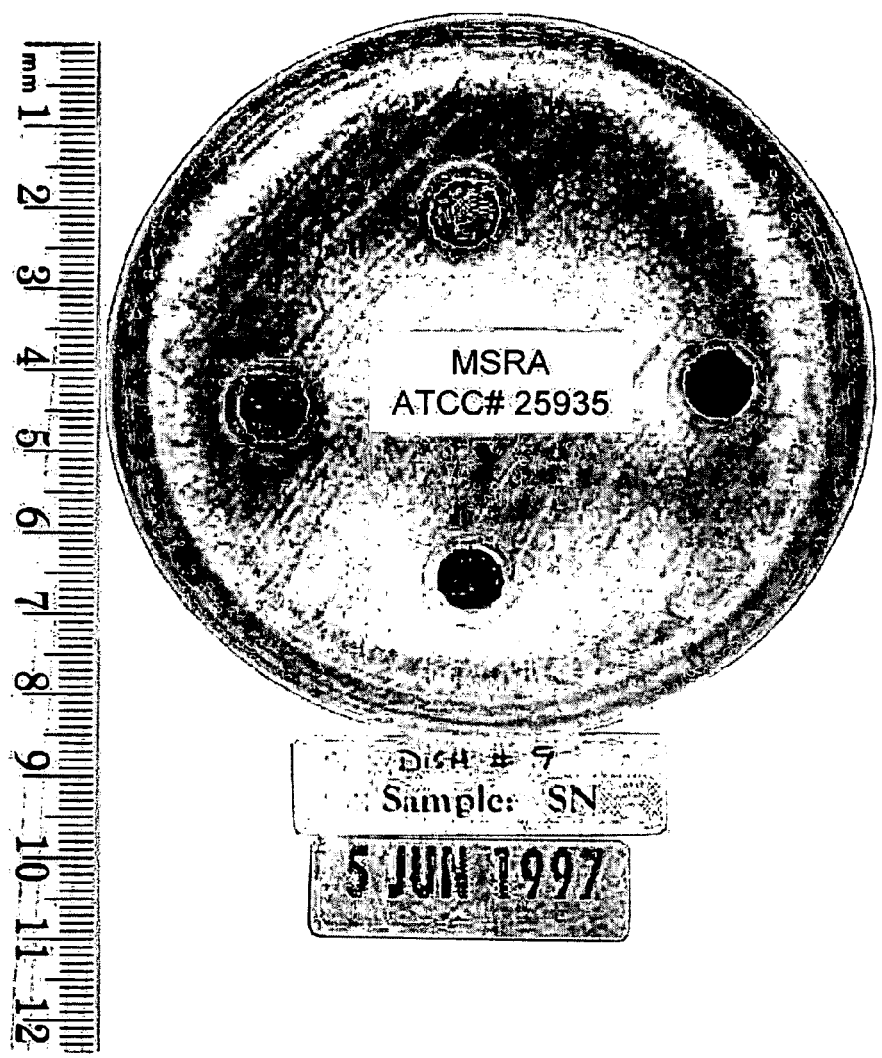

FIG. 8 shows a cup-shaped dressing 80 made from material 10 or 20, usable with a urinary catheter 82. The dressing 80 is fitted over the head of a penis 84 and taped or otherwise attached to the catheter 82.

The present invention can also be used as or in conjunction with an external post-labor and delivery vaginal pad, such as after an episiotomy, or, standard surgical incision. The embodiment is intended for abrasions, lacerations, puncture wounds, partial and full thickness burns, skin tears, traumatic amputations, and dermal ulcerations (vascular, venus, pressure, and diabetic).

The present invention can also be used as a wound drain, where the dressing is a layering of silver containing layers (100% silver-coated nylon fibers) alternating with a non-conductive material, such as, but not limited to, DelNet®. The layering can be two silver plated nylon/nylon, between which is sandwiched a layer of DelNet®. A wound drain preferably has silver coated fiber on both outer surfaces with a layer of nonconducting nylon, polyolefins, rayon, or the like material in between.

Without desiring to be bound by a particular rationale or theory of operation, it is believed that one of the means by which the dressing of the present invention promotes wound healing is by passively delivering silver ions present in the material 10 or 20 to migrate into the wound and the surrounding skin. The silver ions are formed from the passive dissolution of silver in an ionic form from the metallic silver surface. An electrolyte is not required for release of silver from metallic forms-only a liquid. Silver ions are released from the silver coated base fibers by a process called oligodynamic action, i.e., the passive dissolution of silver into a solution. The process was first observed by a Swiss researcher in the 1890's, viz., when metallic silver comes in contact with a water-containing liquid, a small ("oligo-") amount of silver is released into the solution ("dynamic"). Silver is typically not released on a completely dry wound absent other conditions. The foregoing is consistent with the fact that the analgesic effect of a dressing in accordance with the present invention is experienced when applied to a dry wound but the antibacterial effect is not.

Without wishing to be bound by any particular theory, three mechanisms of action may account for the pain relieving aspects of the dressing of the present invention which have been observed and which are documented below. First, the silver creates an antibacterial environment, which in turn diminishes the inflammation caused by the bacteria and subsequently diminishes pain. Second, by separating the layers of silver nylon with a non-conducting material, a capacitative field may be established by the current of injury that is present at the wound surface. Third, as described below, the effect of a highly conductive layer has a positive effect on the electromagnetic field environment of the wound to be healed.

In accordance with early testing, the dressing with the fastest pain relieving aspect was the one with alternating layers of 100% silver nylon and a non-conducting layer, creating a laminate that is eight layers thick with the 100% silver layer against the wound surface. When this dressing is placed against areas of blunt trauma such as contusions, sprains (stretched ligaments), and strains (torn muscles) it also provided pain relief. Laminates having four and six layers provided pain relief but not as rapidly as the eight layer dressing. The fact that the multi laminate provided pain relief when the skin was intact suggests that the pain relieving aspect of the dressing is more an electrical field phenomena, affecting to the alteration in the electric parameters of the skin that accompanies damaged tissue beneath the skin's surface. Later testing discussed below confirms the significance of the electrical effect of the conductive layers of the present invention.

An advantage of the present invention over the prior art is that it does not require an external energy source or galvanic cell action to create and deliver silver ions. The laminate form of the present invention can be utilized to provide a gradient concentration in succeeding layers or within a single layer. Interposing non-conductive layers between conductive layers establishes a capacitive effect which is thought to increase the concentration of the silver ions delivered to the body surface upon which the dressing is placed. The laminate structure 10 or 20 of the present invention can be formed into a number of different useful forms, depending on the particular application and by controlling the permeability of the dressing or by covering the dressing with a membrane of a desired porosity, the proper moisture environment at the treatment site is created and maintained, which further increases silver ion migration.

The present invention exhibits an improved degree of control, compared to previous systems, over the delivery and targeting of silver, viz., by the multiple layers and silver concentration gradient features of the present invention. The pain relieving characteristics of the dressing are also noted. The pain relieving effect is enhanced by making the silver containing layers out of 100% silver nylon.

In contrast to antimicrobial creams and emollients which are gas-impermeable, the dressing of the present invention creates a moist environment with gas permeability that promotes healing by adding a semiocclusive outer layer. The present invention is easier to replace and assists in keeping the wound site clean, rather than having to wash, rinse or otherwise traumatize the site to remove old creams or the like.

The invention will be further described in connection with the following examples, which are set forth for purposes of illustration only. Parts and percentages appearing in such examples are by weight unless otherwise stipulated.

EXAMPLES

Example 1

Laminate of Alternative Layers of Silver and DelNet®

A dressing material was made of three layers. The layer that was against the bacterial culture called "SN" was 100% silver plated nylon woven in a pattern called "warp knit" with individual 15 denier fibers. The next layer, "DK2", was a non-woven 2 oz fabric composed of a mixture of 25% three denier silver plated fibers and 75% three denier rayon fibers. The third layer, "DK8", was a non-woven 8 oz. fabric composed of a mixture of 5% three denier silver plated fibers and 95% three denier rayon fibers. The layers were laminated by needle punch. The ratio of the silver to nonmetalized fiber was as follows for each layer:

| | |
|---|---|
| Layer 1 | 100% silver nylon |
| Layer 2 | 25% silver nylon to 75% nonmetalized fibers |
| Layer 3 | 5% silver nylon to 95% nonmetalized fibers |

The purpose of this Example is to determine the effectiveness of Silver Nylon Fabric Type "SNDK2DK8" with Antimicrobial Disk Susceptibility Testing against four primary organisms that contribute to an infectious process warranting antimicrobial treatment.

The Kirby-Bauer Standard Antimicrobial Suseptibility Test showed that the multilayer SNDK2DK8 was an effective antimicrobial agent for inhibiting bacterial growth. In this test, multilayer SNDK2DK8, control without silver fibers and DK100 (nonwoven single layer 100% silver plated nylon fibers) was tested in broth cultures of selected organisms. The broth is inoculated onto the surface of a Mueller-Hinton agar plate in three different directions. The test sample is then centered on the agar surface and incubated at 35–37° C. for 16 to 18 hours. After incubation, the diameter of the growth free one of complete inhibition including the diameter of the disc is measured to the nearest whole millimeter. The resultant zone of the inhibition is a qualitative indication of antimicrobial activity.

The following organisms were tested:
Escherichia coli ATCC:25922
Pseudomonas aeruginosa ATCC:27853
Enterococcus faecalis ATCC:29212
Staphylococcus aureus ATCC:29213

After the 72 hr. reading, the "SNDK2DK8", DK100 and Control discs were removed with sterile tweezers and moved to a different area of growth on the plate. The plates were placed back into the incubator and reexamined after 144 hrs. The control discs showed no growth inhibition while the SNDK2DK8 showed the greatest inhibition followed by DK100. The E. coli., E. faecalis, and S. aureus plates exhibited no sign of diminished zones of inhibition after the SNDK2DK8 and DK100 disks were removed from the original site. There were no new zones observed around the SNDK2SK8 and DK100 disks when placed in the new area of the plate. However, on the P. aeruginosa plates the zones of inhibition increased from 12 mm to 24 mm in the areas where the disks were removed and new zones of inhibition were formed around the disks after they were moved to a new area of the plate measuring 10 mm/72 hrs.

FIGS. 9–12 are graphs of the foregoing testing.

Clinical Examples

Clinical Case No. 1

FD is a 5 year old female who suffered partial thickness burns to the dorsal aspect of here right foot as a result of excessive sun exposure (sunburn). Antibiotic cream was applied that evening by the parents. Within 24 hours multi laminate silver dressings of the present invention were applied. The patient noted relief of the pain from the partial thickness burn within 30 minutes and slept the entire night pain free. The partial thickness burn healed within twenty four hours. No tattooing or scarring was present.

Clinical Case No. 2

RF is a 41 year old female who suffered partial thickness burns to the volar aspect of her forearm as a result of spilling boiling water on her forearm. The patient was seen in a local emergency room, silvadene cream was applied and analgesics prescribed. Within 48 hours, a multi laminate silver dressing in accordance with the present invention was applied. The patient note relief of the pain of the burn within four hours and did not require any analgesics. She returned to the clinic in three days at which point the wound was completely healed. And the dressings were discontinued. The partial thickness burn healed within 48 hours.

Clinical Case No. 3

Figure 19:
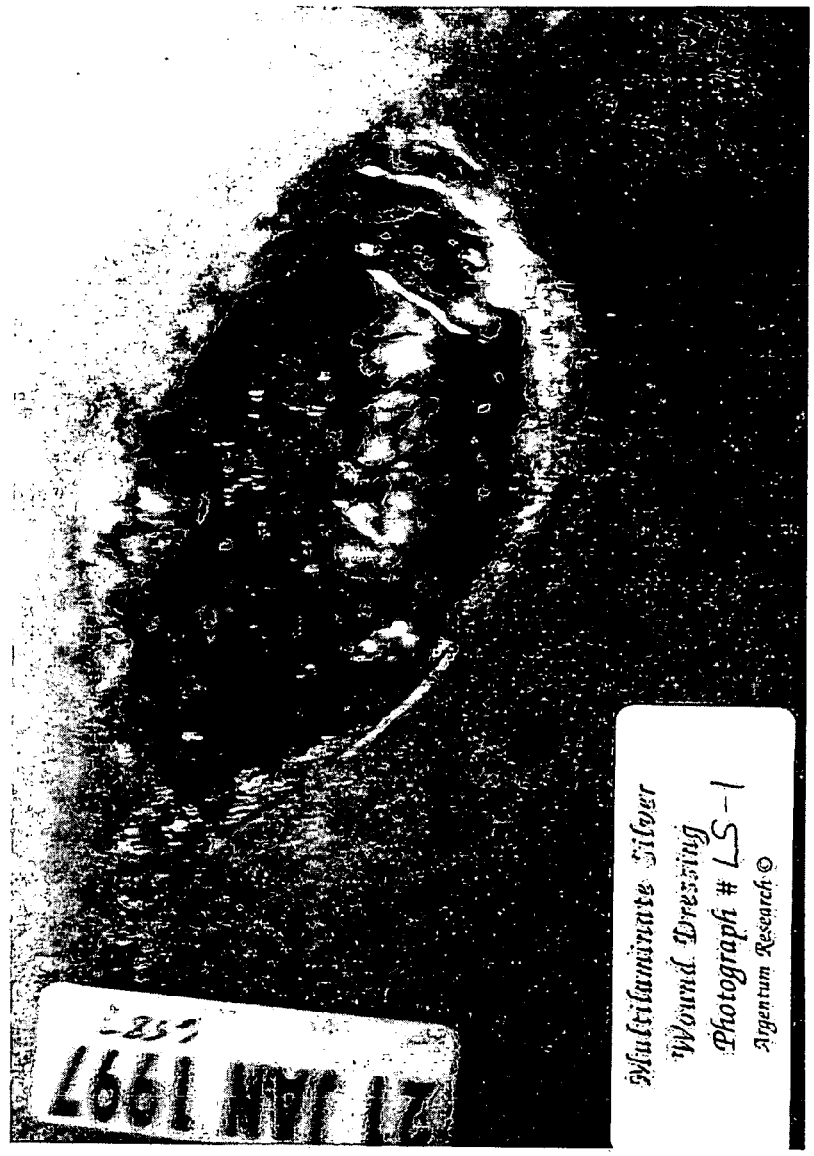
FIGS. 19–24 are photographs of a wound of a patient designated "LS" as taken over a span of several months and showing the healing of the wound treated with a dressing in accordance with the present invention.
Figure 20:
Figure 21:
Figure 22:
Figure 23:
Figure 24:
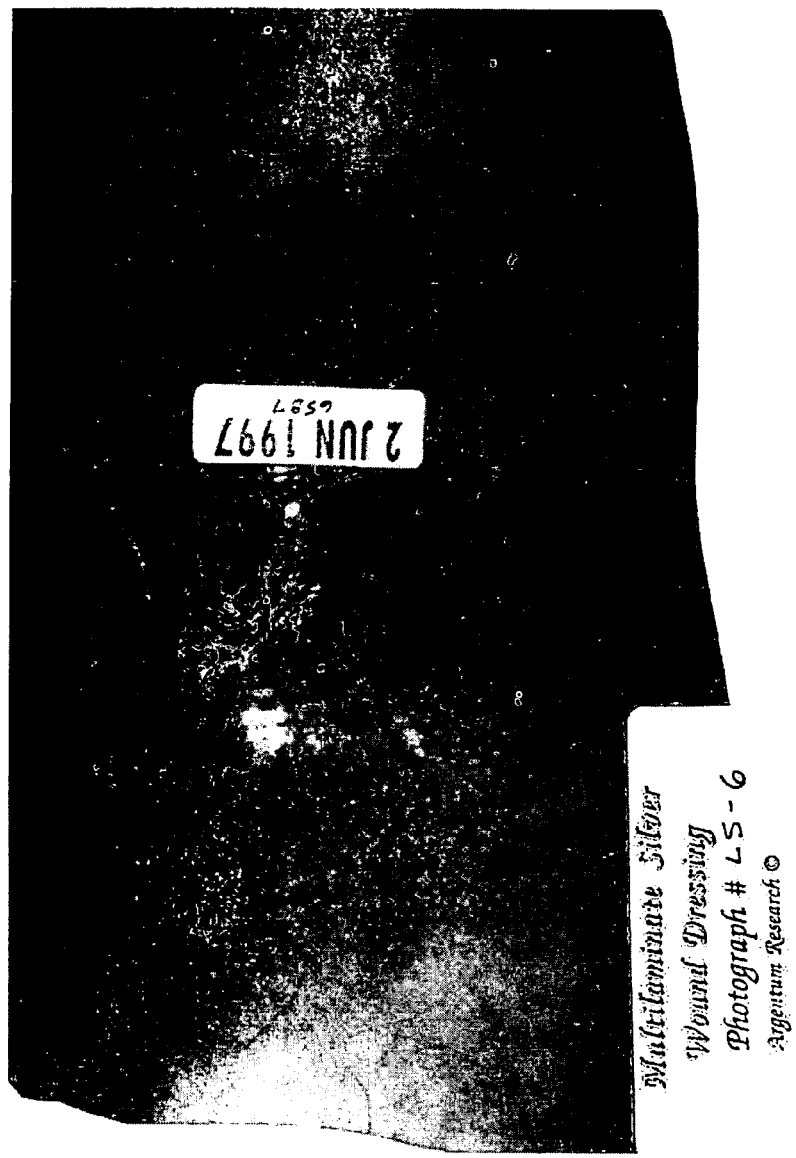

LS is a 44 year old female who suffered a postoperative wound infection and soft tissue breakdown in the popliteal fossa (back of knee). The day the dressings were initiated was noted in photograph No. LS-1 (See FIG. 19). Photograph No. LS-2 (See FIG. 20) was taken twelve days later with daily dressing changes. The patient noted that within forty-eight hours the wound was essentially pain free with the exception when the dressing was changed and the wound was uncovered. Photograph Nos. LS-3, LS-4 and LS-5 (FIGS. 21–23) show progressive wound healing. Photograph No. LS-6 (FIG. 24) shows the wound healed.

Clinical Case No. 4

Figure 25:
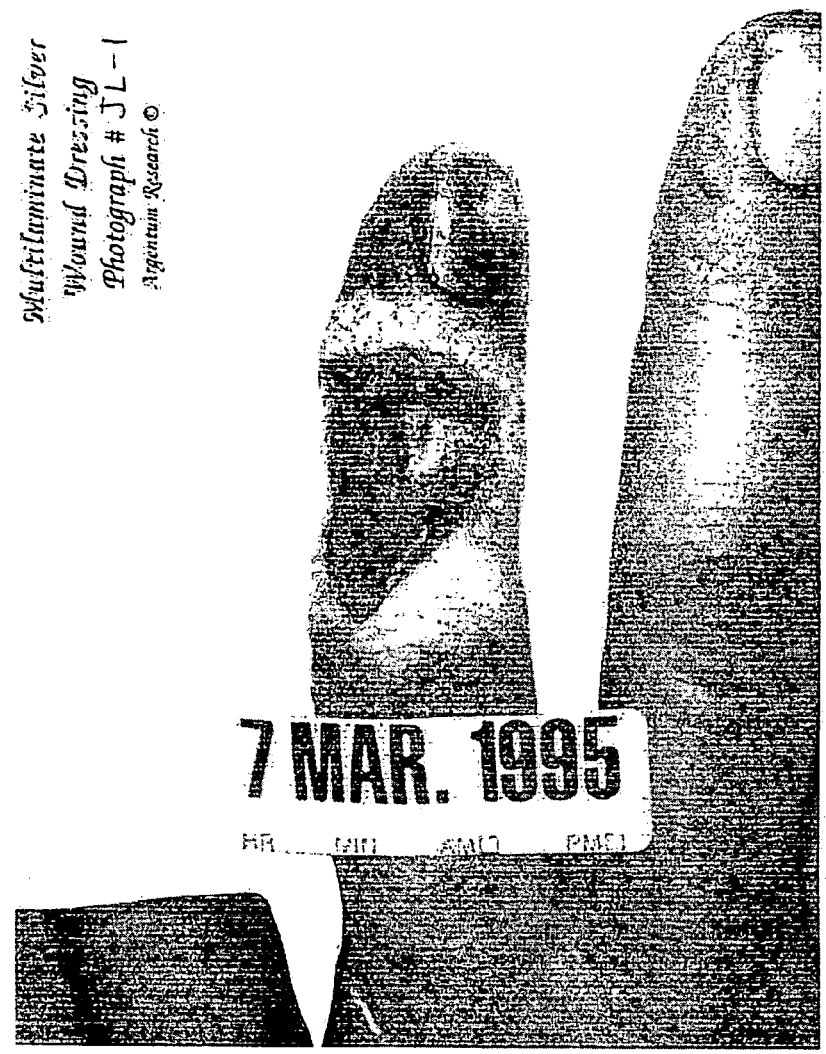
FIGS. 25–29 are photographs of a wound of a patient designated "JL" as taken over a span of several months and showing the healing of the wound treated with a dressing in accordance with the present invention.
Figure 26:
Figure 27:
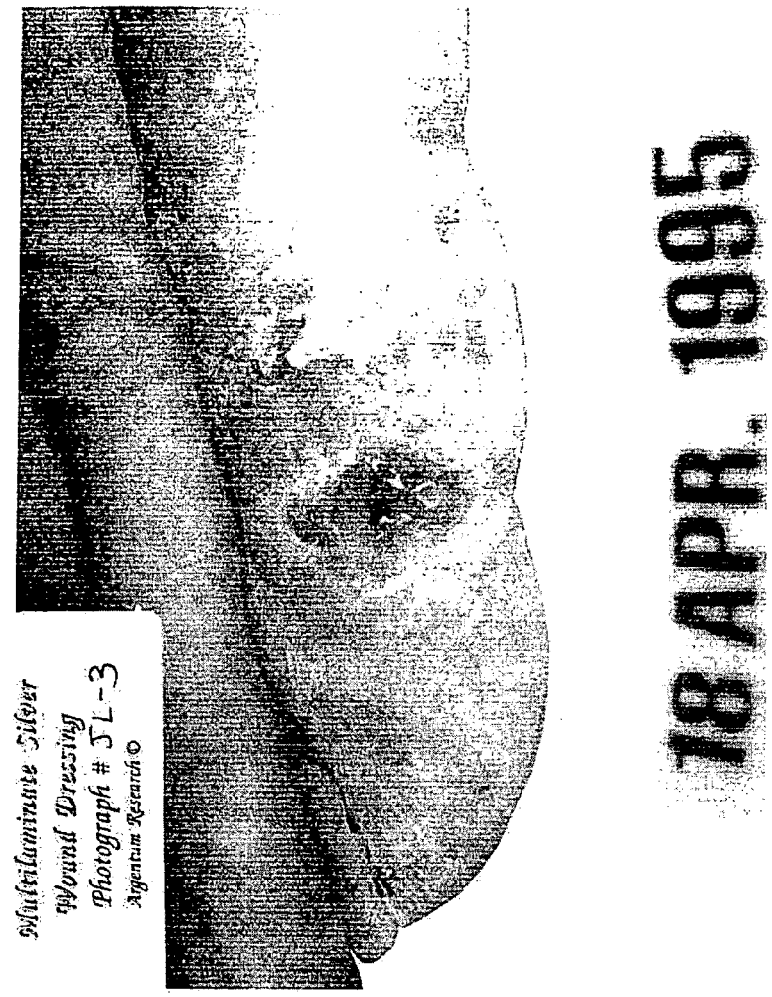
Figure 28:
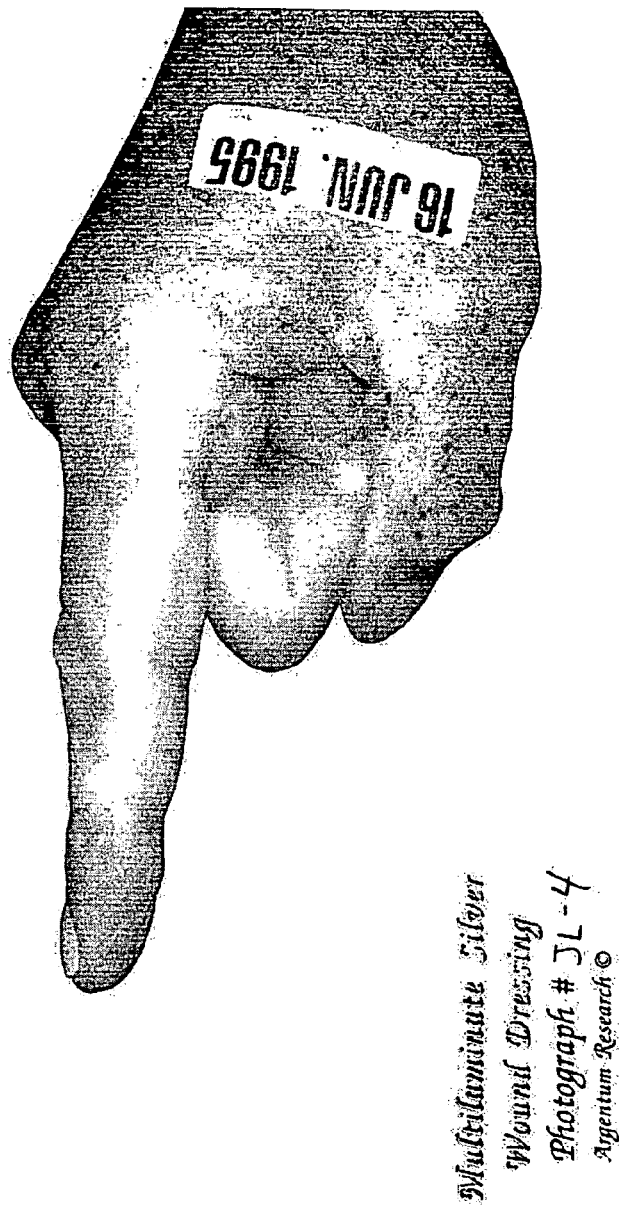
Figure 29:

JL is a 46 year old female who suffered a sharp laceration to the radial aspect of her index finger. Soft tissue was lost that extended down to the tendon (Photograph No. JL-1) (See FIG. 25). Dressings were changed on a daily basis. Photograph Nos. JL-2 and JL-3 (see FIGS. 26 and 27) show progressive wound healing. The patient noted that the wound was pain free after 48 hours. At the completion of wound healing (Photograph Nos. JL-4 and JLS) (See FIGS. 28 and 29), the patient noted full range of motion of the digit with normal sensation to light touch.

The results of the foregoing Examples show that the multilayer laminate of the present invention clearly provides significantly improved benefits over a single layer dressing. While prior dressings may have incorporated more than one layer, they only contemplate the use of a single layer of silver-coated fibers. An unexpected result of the present invention is that multiple layers of silver, particularly where the layers are separated by nonconductive layers of material, provide improved silver ion migration and improved healing, antibacterial and antifungal properties.

The above described laminate structures, i.e., laminates of successive layers containing different ratios of metalized fibers to non-metal fibers and laminates with alternating layers of conductive and non-conductive fibers result in enhanced wound healing as well as provide an analgesic effect. The inventor has discovered that creating a laminate of one or more plies of a highly conductive metal or metal coated fabric has shown to be highly effective demonstrating a pronounced analgesic and wound healing effect on biological tissues even absent alternating nonconductive layers. The inventor has discovered that the passive conductivity of a highly conductive dressing is a key factor in promoting healing of biological tissues. The greater the conductivity of at least one layer of the laminate the greater the analgesic effect reported on injured tissue. The analgesic effect is most pronounced on acute injuries but is also present on chronic lesions. With highly conductive dressings in accordance with the present invention, metal ion flow is not required to produce the analgesic properties of the appliance and improve tissue healing characteristics. The dressing can even be placed several millimeters above the wound and still exhibit analgesic and healing effects. Ion flow is, however, required for the antimicrobial effect.

This second type or class of dressing appliance described below is typified most completely by a highly conductive material that when placed on the wound surface or on the skin overlying the areas of soft tissue or osseous injury, assists with the healing of the involved tissues and provides an analgesic effect. The dressing affects the electrical potentials in and around the tissue injury site. The electrical parameters promoting healing and analgesic are reestablished passively. The effectiveness of the embodiment rests with the maximizing of conductivity and minimizing of resistance of the dressing.

Figure 30:
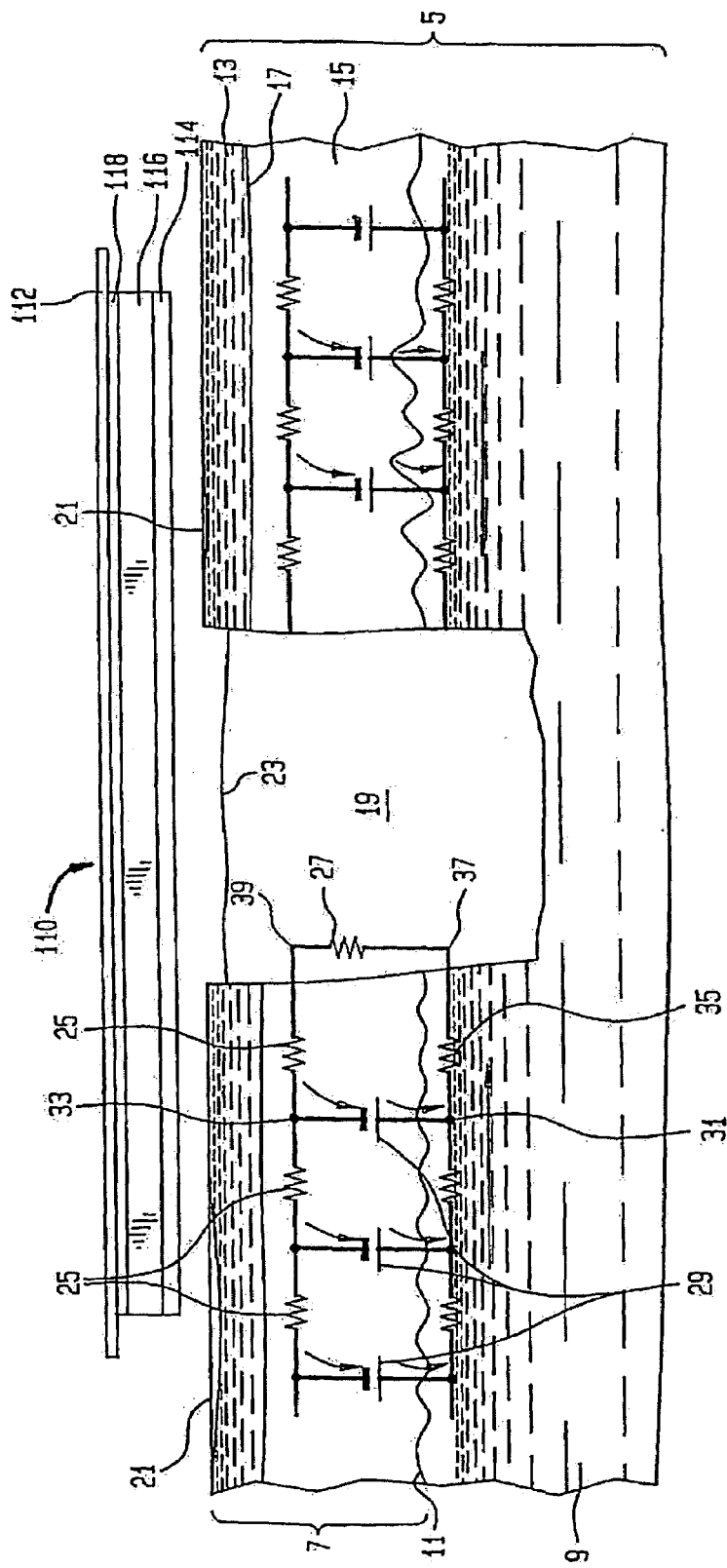
FIG. 30 is a schematic depiction of a cross-section of wounded mammalian skin with a dressing in accordance with a tenth embodiment of the present invention positioned over the wounded area.

FIG. 30 is a cross sectional representation of typical mammalian skin 5 with an electrical circuit generated by the TEP overlayed on the anatomy. The epidermis 7 overlies the dermis 9 at junction 11 and includes the stratum corneum layer 13 and the stratum spinosum layer 15 with junction 17 therebetween. The stratum corneum layer is composed of dead cornified squamous epithelium. The space 19 represents a wound that is filled with both cellular and dissolved elements of the blood including fibrinogen, fibronectin, polymorphonuclear leukocytes, platlets and red blood cells. The surface 21 of the skin distal to the wound 19 can be expected to have a potential in a range of from −10 to −70 milivolts (depending on the location on the body) due to the TEP. The potential on the surface of the wound is designated by reference no. 23. The resistance of the return paths of the current induced by the epidermal battery is represented by resistors 25. The resistance of the wound is represented at 27. The epidermal battery is represented by symbols 29. A dressing 110 in accordance with the present invention and having highly conductive layer 114, absorbent layer 116, semipermeable layer 118 and tape layer 112 is shown proximate the wounded skin surface 21. Prior to placement of dressing 110 on the wound 19, the wound potential, e.g., at 23, is more positive than on the surface of the skin, e.g., at 21. That is, the surface potential becomes less negative and can in certain instances become positive. This is due to the removal of the epidermal battery 29 at the wound 19. The further potential test point 23 is from the unwounded surface 21, the more closely the potential at 23 will approximate the potential of the positive side of the battery 29. If the wound 19 is wet and therefore conductive, a current between points 31 and 33 will be induced by the TEP, i.e., the wound current. The wound current will pass through the exudate filling the wound 19 along the most efficient (lowest resistance) path available, most likely proximate the edge of the wound, as this will be the shortest path and the most moist path. The resistance to the wound current is represented by resistance 27. The wound current will pass from point 31 through the resistance at the junction 11 represented by resistor 35 into the wound at point 37 through the wound resistance 27 to point 39 where it reenters the epidermis 7 at the junction 17 through the resistance of junction 17 represented as resistor 25 to point 33 on the other side of battery 29.

When the dressing 110 is placed on the wound 19, the conductive layer 114 lowers the potential of the wound, e.g., at 23 by virtue of electrical contact with uninjured skin surfaces at 21 which have a negative potential established by the epidermal battery 29. The dressing 110 lowers the potential of the wound surface, e.g., at 23 and provides a conductive bridge between healthy skin surfaces 21 on either side of the wound 19. The point of maximum resistance shifts from point 39 to point 37. This in turn shifts the point of maximum lateral potential drop from point 39 to point 37. With the shift in lateral potential, the electrical characteristics of the wound more closely resemble the amphibian wound than the mammalian wound. It is because of this shift caused by the highly conductive surface embodied in dressing 110 that wound healing is accelerated. The shift in lateral potential also reduces the amount of stimulation that superficial nerve endings receive, thereby creating the analgesic effect that is noted clinically. It should be appreciated that the moisture retention of dressing 110 augments the foregoing process by retaining moisture in the wound to further reduce wound resistance 27 and assists with the shift in lateral potential to deeper structures. Without the present invention, resistance 27 is high, little or no current flows in the wound and little or no lateral field exists at the edge of the wound to stimulate healing.

Figure 31:
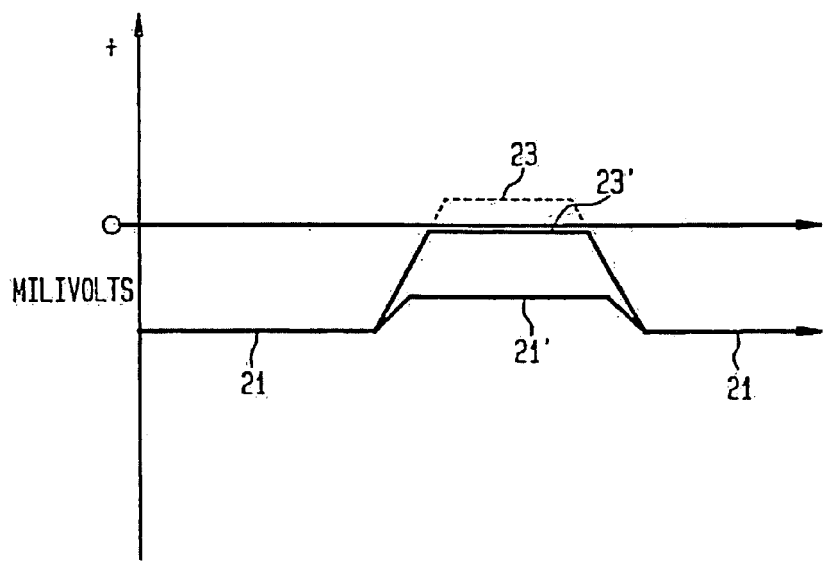
FIG. 31 is a graph of voltage verses position on the wounded skin as shown in FIG. 30.

FIG. 31 is a representative graph of the voltage at the surface of human skin as one proceeds from normal skin, 21, to the open wound, 23, to normal skin again. The area of normal skin 21 measures a relatively constant negative voltage between 10 and 70 milivolts. The area of the wound surface where the TEP and the epidermal battery is disrupted at 23 is always more positive than uninjured skin 21, reaching voltages between 23' and 23. When a dressing 110 in accordance with the present invention is applied and the wound is kept moist, it is possible to return to more normal skin potentials as shown at 21' on the graph. The present invention reestablishes a TEP via a redistribution of surface potential.

Figure 32:
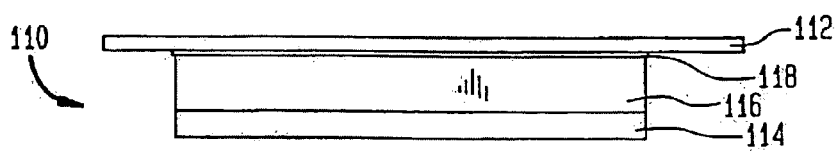
FIGS. 32–35 show various laminar structures associated with eleventh through fourteenth embodiments of the present invention.

FIG. 32 reveals the configuration of a standard composite wound dressing 110. Layer 114 is a multi-ply or single layer of highly conductive material that may be pure metal, combinations of metals, or metal coated fibers. Layer 116 is an absorbent layer that may be composed of a foam or sponge-like material, such as, cotton, rayon, polyvinyl alcohol, polyvinyl acetate, polyethylene oxide, polyvinyl pyrrolidon, polyurethane hydrocolloids, and alginates. Layer 118 is a semipermeable breathable urethane barrier film. Layer 112 is an adhesive bandage similar to polyester spun-laced apertured non-woven fabric coated on one side with an acrylic pressure sensitive adhesive.

The conductivity of layer 114 is critical to the invention and is dependent on: (1) the material; and (2) the configuration of the material composing the dressing. The key characteristic of the material composing the dressing is the material's conductivity or the number of free electrons that the material can provide. The configuration of material composing the conductive layer 114 is concerned with: (1) the manner in which the conducting material is coated on to substrates; (2) the geometry of the individual fibers; and (3) the construction of the layer 114.

Metals are generally recognized as the best conducting materials with the largest quantity of free electrons. Solid metallic wire-like embodiments have proven to provide excellent conductivity. Reviewing the properties of metals as conductors, the volume resistivity values are:

| | |
|---|---|
| Silver | $1.59 \times 10^{-6}$ ohm-cm |
| Gold | $2.22 \times 10^{-6}$ ohm-cm |
| Aluminum | $2.65 \times 10^{-6}$ ohm-cm |
| Nickel | $6.03 \times 10^{-6}$ ohm-cm |
| Tin | $11.0 \times 10^{-6}$ ohm-cm |
| Stainless Steel | $100 \times 10^{-6}$ ohm-cm |
| Graphite | $1375 \times 10^{-6}$ ohm-cm |
| Copper | $1678 \times 10^{-6}$ ohm-cm |
| Conductive Polymers | $10,000 \times 10^{-6}$ ohm-cm |

Other metals such as metallic alloys also have excellent conductivity. Resistivity values vary based upon the relative percentages of each metal. The ranges of resistivity are:

| | |
|---|---|
| Aluminum—Copper | 2.74 to $11.2 \times 10^{-6}$ ohm-cm |
| Aluminum—Magnesium | 3.18 to $13.4 \times 10^{-6}$ ohm-cm |
| Copper—Gold | 2.45 to $14.1 \times 10^{-6}$ ohm-cm |
| Copper—Nickel | 2.85 to $50.1 \times 10^{-6}$ ohm-cm |
| Copper—Palladium | 2.92 to $6.1 \times 10^{-6}$ ohm-cm |
| Gold—Palladium | 2.86 to $27.6 \times 10^{-6}$ ohm-cm |
| Gold—Silver | 2.75 to $10.4 \times 10^{-6}$ ohm-cm |
| Iron—Nickel | 12.0 to $33.9 \times 10^{-6}$ ohm-cm |
| Silver—Palladium | 3.70 to $40.6 \times 10^{-6}$ ohm-cm |

From the perspective of conductivity, silver is the ideal metal to utilize in layer 114 based upon the fact that it has the lowest volume resistivity. (The salts of silver as well as the silver complexes, both organic and inorganic, are very poor conductors and essentially act as dielectric insulator materials. The prior art utilizing silver and silver compounds has focused primarily upon the ability of the metallic surface to provide silver ions rather than electrical conductivity.) Ionic silver has the added benefit of exhibiting significant antimicrobial action with minimal potential for allergic reactions.

Conductive gels, conductive pastes, and elastomers such as rubberlike silicon in which suspended metal particles are present may be used in layer 114. Superconductive alloys and compounds would also be excellent to use if the superconductivity were possible at room temperature.

Metallic coated surfaces on elastomeric substrates have been found to provide excellent conductivity. The metal can be coated onto the base fiber by spraying, vapor deposition, dipping or other techniques known to those skilled in the art. The technique that provides the greatest conductance and lowest resistance has been shown to be autocatalytic electroless plating. Suitable elastomeric substrates for use in the present invention include but are not limited to: nylon, fiberglass, cotton, silk, polyvinyl alcohol, polyvinyl acetate, polyethylene oxide, polyvinyl pyrrolidone, polyurethane, and rayon. The metal coating formed on a substrate may be applied by vapour deposition techniques such as vacuum evaporation, sputtering, magnetron sputtering, ion plating or autocatalytic chemical electroless plating. To achieve a high conductivity, the metal coating technique of choice is autocatalytic electroless plating. This process is based on the catalytic reduction of metal salts to produce the plated metal in its elemental form. This plating technique tends to provide an even coating because the metal does not build up on the edges of the sample. Electroless plating covers the entire surface of the substrate and fills in crevices and sharp corners, to deposit a coating of equal thickness on the entire sample. The purity of the substrate to be plated is very important in achieving uniformity of metal coating. The higher the purity of the metal coating the better the conductivity. The percentage of silver that is plated can vary from 1% to 40% by weight. Before acceptable conductivity is achieved, the percentage of silver should be 10% by weight. The ideal plating percentages run between 14% and 20%. Above 20% there is little improvement in conductivity with increasing silver content.

The thickness of the metal coating also affects conductivity. Acceptable levels of conductivity are achieved with coatings greater than 0.2 micrometers. The ideal coating thickness is between 0.4 micrometers and 1.2 micrometers. As noted, the purity and uniformity of metal coating on elastomeric substrates is best achieved by the autocatalytic electroless plating process. Electroless silver plating essentially involves the mirroring reaction also known as the Tollens Test expressed in the following form:

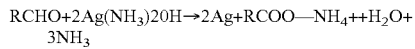
RCHO+2Ag(NH$_3$)20H→2Ag+RCOO—NH$_4$++H$_2$O+ 3NH$_3$

Electroless plating baths are designed such that when a catalyzed substrate is introduced into the plating bath, deposition of the metal begins in a slow and even manner. Once the process is initiated, the plating solution will continue to plate because the deposited metal catalyzes its own its own electroless plating, thus making the reaction autocatalytic.

The conductivity of various materials prepared in accordance with the present invention is presented in Table I below. In all cases, the autocatalytic plating process was superior to the vapour deposition process, the silver phosphate glass composition, and the silver ion beam process in producing highly conductive material. The vapour deposition process, the silver phosphate glass composition, and the silver ion beam process produce a non-uniform coating of metal on substrate. The vapour deposition process is the better of the three but still has limitations due to the lack of uniformity and continuity of the plating process. As anticipated, pure metal screening has excellent conductance but lacks the requisite softness and pliability that would enable it to be preferred for use in wound dressings. Accordingly, metallized flexible fibers such as nylon are preferred for such applications. Additional suitable fibers are identified in the preceding description of laminate embodiments of the present invention. In addition to the selection of fiber and metallic coating, the shape of the fibers (and resultant coated fibers) and their integration into a layer, e.g., by weaving, knitting, etc., play a large part in the resultant conductivity of the layer 114.

The various cross-sectional shapes that may be imparted to individual fibers are known to those skilled in the art. Generally recognized cross-sectional shapes are: round, oval, kidney-bean, dogbone, flat, trilobal, and multilobal. For the purposes of the present invention, the greater the amount of surface area that is metal plated with a uniform thickness, the greater the conductivity. Fibers with denier size between 1 and 80 show excellent conductivity.

Individual fibers may be fabricated into several different types of yarns: spun yarns; filament yarns; compound yarns; and fancy yarns. The filament and compound yarns that exhibit multiple longitudinal filaments exhibit the greatest conductivity. The greater the continuity of the yarns, the greater the potential for excellent conductivity when plated.

Fibers and/or yarns are assembled into fabrics: woven fabrics, twisted and knotted fabrics, knit fabrics, nonwoven fabrics, and compound/complex fabrics. The inventor has found that the total surface area of the fibers that compose the fabric is an important variable in determining conductivity. The manner in which the fibers interact and touch each other also influences conductivity. The present invention recognizes that a plurality of metallized fabric plies can be stacked and/or joined together to decrease the resistance of the composite multi-ply conductive layer 114. The resistance per unit surface area (one to four plies) of representative samples of the major fabric categories is summarized in Table 1 below. In the knitted fabric line, utilizing the autocatalytic silver plating technique, double rib knit with central pile, tricot jersey knit, warp knit, and tricot warp knit were evaluated. In all cases, as the thickness of the layer increased, the resistance decreased per unit area. The knit fabrics that could be stretched (tricot jersey knit, warp knit, and tricot warp knit) noted a small reduction in resistance when placed under tension. Although all knit products preformed very well, the double rib knit with central pile performed the best at one ply. The one ply double rib knit contained approximately the same amount of silver as four plies of the tricot jersey knit. The double ply of this rib knit provided excellent continuity and fiber contact.

In the woven fabric line, the rip stop, plain weave, and pile weave all showed reduction in resistance as plies were added. The pile weave exhibited excellent conductivity even with one ply. The rip stop had more fibers per unit area and therefore greater conductivity.

In the spun bond nonwoven pattern, the conductivity was excellent with progressive reduction in resistance as more plies are added.

For the purposes of the present invention, the criteria of fabric design lies primarily with the resultant conductivity of the material. The discussion below will be focused (as an example, not as a limitation) on the use of a fiber matrix, but it is to be understood that other ply structures are contemplated as within the scope of the present invention. It is preferable that the fabric be medical grade with minimal dermal reactivity or sensitivity as well as non cytotoxic. The plies can be made of the same material, different materials, or, can comprise two or more materials.

The fabric can be made of pure conductive material or a base fiber coated or otherwise containing the conductive material. For example, the fabric base material can be made of nylon, polyethylene, polypropylene or other polymer, fibers of which are formed by meltblown, spunbond, spincasting or other techniques known to those skilled in the art and appropriate for the particular coating material and laid down as a mat on a foraminous web. Alternatively, threads or fine extruded wire strands can be woven into a web structure. Conductive material can be incorporated into the base material during the fiber or the web forming process, such as by conforming, bicomponent extrusion, or the like. A preferred material is silver-coated nylon fiber.

It is preferable that the fabric material in each layer have a resistance of

Broad Range: 1,000 ohms/in$^2$ to 0.0001 ohms/in$^2$;
Middle Range: 10 ohms/in$^2$ to 0.001 ohms/in$^2$
Optimal Range: 0.1 ohms/in$^2$ to 0.01 ohms/in$^2$.

Resistance decreases with increasing numbers of plies or fibers within a layer. Beyond four plies of conductive fabric, the resistance decrease becomes nonappreciable from a clinical point of view although the resistance continues to decrease with additional layers. The practical upper limit of the conductive plies is ten. Also, cost, thickness, composition, fiber density and weave structure and other factors may limit the number of plies. A denser fabric design may need only one ply to achieve the same resistance measurement as more than one ply of a highly absorbent, less dense material. This was seen with the pile woven and the double rib knit reported in Table 1. The key to reducing the resistance of the conductive layer 114 lies primarily in the manner in which the fabric is. plated and secondarily in how the layer 114 is constructed. Fabrics where the fibers are continuous or even melted together generally have lower resistance with greater continuity of the metallic layer. The larger the surface area of fiber contact the better the conductivity and the lower the resistance.

One means for laminating and electrically integrating the plies is by point embossing or point bonding achieved by passing the fabric between a pair of niprolls, one roll having a series of spaced apart pins extending radially from the roll, and the other roll being flat. As the fabric plies are passed between the niprolls the pins press into the plies and force the fibers of one ply into the interstices of the next ply, thus bonding the two plies by fiber-to-fiber interaction forces. Alternatively, the plies can be laminated by adhesives, spot bonding (by ultrasonic welding or laser welding) or other techniques known to those skilled in the art. The optimal technique for laminating the plies is sewing them together with conductive thread preferably autocatalytic silver nylon plated poly or monofilament silver nylon thread. The conductive laminating thread enhances the overall conductivity of the conductive layer 114 and minimizes the resistance.

The fibers of the nylon fabric enhance continuity of the metal plating, thereby increasing conductivity. When the conductive layer 114 is composed of fabrics that can be stretched, the metal plated nylon is wrapped around elastic fibers so as to provide optimal conductivity as the fabric is stretched.

Other materials can be incorporated into the fabric, such as, but not limited to, antibiotics, fungicides, topical anesthetics, desiccants or absorbents, materials designed to wick fluid away from the wound site, materials designed to retain moisture or fluid, microencapsulated materials for prolonged or selective release into the wound area, and the like.

Clinically, it has been observed that the lower the resistance of the conductive layer 114, the faster the pain relief, the faster the wound healing and the greater the edema reduction. Accordingly, the present invention provides a dressing that stimulates healing of the underlying tissues and provides an analgesic effect. In order for the dressing 110 to provide its beneficial effect over an acceptable period, means must be provided to maintain high conductivity that persists over an extended period of time and in the presence of wound exudate, body sweat or bodily fluid discharges. In order to achieve this objective of long duration conductivity, several constructions are presented herein, namely, the conductive layer 114 can be: (1) a multi-ply laminate having a plurality of plies of conductive material, preferably in electrical continuity at numerous points of contact or (2) a conductive layer 114 with multiple internal conductive fibers that provides the same conductivity as the multi-ply laminate. As noted, the conductive layer 114 may be part of a multilaminate wound dressing that includes some or all of the following layers: (1) Conductive layer; (2) Absorbent layer; (3) Vapour and non-strick through layer; (4) tape or adhesive layer. The conductive layer may be positioned against the wound surface or isolated from the wound surface by a semipermeable membrane. In addition, two or more conductive layers may be included in the same dressing. The conductive layer 114 can also be attached to an orthopaedic brace or an orthopaedic cast. In such applications, it is useful to employ the following laminar structure: (1) Conductive layer; (2) Padding layer; (3) Adhesive layer.

The conductive layer 114 preferably includes a flexible conductive material which can be a fabric or mesh, either woven fabrics, knitted fabrics, twisted and knotted fabrics, nonwoven fabrics, or compound/complex fabrics, or as long as conductivity is maintained. For braces and splints the conductive layer 114 need not be flexible and may be rigid, semi rigid, or flexible.

The multilayer laminate 110 or the conductive layer 114 alone can be manufactured into a number of wound dressing products, such as, bandage strips, wraps, pads, butterfly bandages, multilayer island and strip composite wound dressings, external body coverings, near or next to the dermis for blunt trauma or fractures, oral, vaginal, rectal, nasal, ear canal suppositories, napkins and inserts, shoe orthotics, liners for braces, bra liners, external feminine napkins, catheter tube sleeves, and wound drains.

As noted above, increasing the number of plies in the conductive layer 114 improves duration of high conductivity. The multi-plies allow the conductivity to stay high as the dressing stays in contact with the wound. As the ply or plies of dressing closer to the wound increase their resistance secondary to the formation of silver chloride crystals, the additional plies electrically contacting these wound contacting plies maintain the conductivity whereas the conductivity of a single ply would be substantially reduced. In a similar vein, multiple plies maintain conductivity despite sweat from the dermis containing chloride ions that would otherwise reduce the conductivity of wraps that are place for closed injuries such as bone fracture, ligament or muscle tears, soft tissue contusions.

If a highly conductive layer 114 is employed, alternating nonconductive layers and gradient of ion concentration features may be eliminated which reduces the cost and bulk of the dressing. While silver is the preferred coating metal due to its high conductivity, any conductive material may be used, expensive silver-containing fabric is therefore not required.

Tests were preformed on the conductive plies of the conductive layer 114 to look for various electrical properties of static and/or dynamic electrical fields, capacitive effects, inductive effects, and conductivity. The materials did not exhibit any capacitive or inductive effects even when placed in stacked plies (but in contact with each other). With both AC and DC signals applied to these plies, no unusual electrical characteristics could be found. The only measurable effect was the conductivity. The fabrics had very low contact resistance, with non-uniform surface conductivity. The non-uniformity was a function of the weave design, the direction of measurement, and the tension applied to the material.

In order to make accurate and repeatable measurements of the samples, a Fabric Holding device was fabricated with a nylon substrate. Brass hold down clamps were precisely spaced with a gap between the plates of 1.00 inch. Since similar materials are used on both ends of the fabric clamps, any dissimilar metal effects between the fabric and the clamp would be canceled out. The fabric samples were cut to 1.00 inch width and 1.25 inch long in both directions of the samples' weave, and placed under the clamps providing a square inch of exposed material that was tested. The resistance of the sample was measured using a 4½ digit multimeter (resolution of 0.01 ohms). The basic accuracy of the device is +−0.02 ohms. All measurements were corrected for the test lead resistance and meter contact resistance.

The measurements were made with the samples lying flat on the fabric holding device without tension placed on the material. To provide a measurement under tension, the non-stressed material was elevated (while maintaining tightness on the clamps) between the hold-down clamps with a wedge that lengthened the 1.00 inch gap between the clamps to 1.10 inches. This 10% elongation was used for the measurements under tension.

Measurements were limited to silver containing plies. The conductivity (units of ohms per square inch) of the autocatalytic plated, vapor deposited plated, ion beam plated, silver salt porcine skin chemical deposition and pure metallic silver in foil and sheet form is presented Table 1.

TABLE I

| Tricot Jersey Kint Autocatalytic Plated Silver Nylon .9 ounces silver/m2 | | | | |
|---|---|---|---|---|
| Measurement Along | 1 Layer | 2 Layers: sewn | 3 Layers: sewn | 4 Layers: sewn |
| Warp Direction | 0.68 W/in$^2$ | 0.38 W/in$^2$ | 0.22 W/in$^2$ | 0.15 W/in$^2$ |
| Weave Direction | 0.88 W/in$^2$ | 0.44 W/in$^2$ | 0.30 W/in$^2$ | 0.22 W/in$^2$ |
| Alternating Direction | | 0.39 W/in$^2$ | 0.24 W/in$^2$ | 0.17 W/in$^2$ |
| Warp Under Tension | 0.51 W/in$^2$ | | | |
| Weave Under Tension | 0.70 W/in$^2$ | | | |
| Measurement Along | 1 Layer | 2 Layers: glue | 3 Layers: glue | 4 Layers: glue |
| Warp or Weave | 0.67 W/in$^2$ | 0.40 W/in$^2$ | 0.28 W/in$^2$ | 0.20 W/in$^2$ |
| Warp Knit Autocatylitic Plated Silver Nylon 4.0 ounces silver/m$^2$ | | | | |
| Measurement Along | 1 Layer | 2 Layers: sewn | 3 Layers: sewn | 4 Layers: sewn |
| Warp Direction | 0.72 W/in$^2$ | 0.38 W/in$^2$ | 0.25 W/in$^2$ | 0.17 W/in$^2$ |
| Weave Direction | 2.12 W/in$^2$ | 1.05 W/in$^2$ | 0.75 W/in$^2$ | 0.55 W/in$^2$ |
| Alternating Direction | | 0.55 W/in$^2$ | 0.45 W/in$^2$ | 0.30 W/in$^2$ |
| Warp Under Tension | 0.56 W/in$^2$ | | | |
| Weave Under Tension | 2.51 W/in$^2$ | | | |
| Non-Woven 8 Ounce Autocatylitic Plated Silvery Nylon | | | | |
| Non-Woven | 1.05 W/in | 1.00 W/in$^2$ | 0.80 W/in$^2$ | 0.70 W/in$^2$ |
| Double Rib Knit with Central Pile Autocatylitic Silver Nylon 4.0 Ounce/m$^2$ | | | | |
| Warp Direction | 0.20 W/in$^2$ | 0.15 W/in$^2$ | 0.12 W/in$^2$ | 0.10 W/in$^2$ |
| Weave Direction | 0.20 W/in$^2$ | 0.15 W/in$^2$ | 0.12 W/in$^2$ | 0.10 W/in$^2$ |
| Spun Bonded Autocatylitic Plated Silver Nylon 1.0 Ounce Silver/m$^2$ | | | | |
| Warp Direction | 0.38 W/in$^2$ | 0.30 W/in$^2$ | 0.27 W/in$^2$ | 0.20 W/in$^2$ |
| Weave Direction | 0.38 W/in$^2$ | 0.30 W/in$^2$ | 0.27 W/in$^2$ | 0.20 W/in$^2$ |
| Conductive Film Polyruethane and Autocatylitic Plated Silver Nylon | | | | |
| Staple/fiber Side | 1.50 W/in$^2$ | | | |
| Rip Stop Weave Autocatylitic Plated Silver Nylon 2.2 Ounce Silver/m$^2$ | | | | |
| Warp | 0.30 W/in$^2$ | 0.22 W/in$^2$ | 0.18 W/in$^2$ | 0.16 W/in$^2$ |
| Weave | 0.30 W/in$^2$ | 0.22 W/in$^2$ | 0.18 W/in$^2$ | 0.16 W/in$^2$ |
| Plain Weave Autocatylitic Plated Silver Nylon 2.2 Ounce Silver/m$^2$ | | | | |
| Warp | 0.60 W/in$^2$ | 0.50 W/in$^2$ | 0.40 W/in$^2$ | 0.30 W/in$^2$ |
| Weave | 0.60 W/in$^2$ | 0.50 W/in$^2$ | 0.40 W/in$^2$ | 0.30 W/in$^2$ |
| Tricot Warp Knit Autocatylitic Plated Silver Nylon 1.5 Ounce Silver/m$^2$ | | | | |
| Warp under Tension | 0.40 W/in$^2$ | 0.30 W/in$^2$ | 0.20 W/in$^2$ | 0.20 W/in$^2$ |
| Warp without Tension | 0.30 W/in$^2$ | 0.20 W/in$^2$ | 0.20 W/in$^2$ | 0.20 W/in$^2$ |
| Weave under Tension | 0.40 W/in$^2$ | 0.30 W/in$^2$ | 0.20 W/in$^2$ | 0.20 W/in$^2$ |
| Weave without Tension | 0.30 W/in$^2$ | 0.20 W/in$^2$ | 0.20 W/in$^2$ | 0.20 W/in$^2$ |
| Pile Woven Autocatylitic Plated Silver Nylon 4.0 Ounce Silver/m$^2$ | | | | |
| Warp | 0.20 W/in$^2$ | 0.15 W/in$^2$ | 0.15 W/in$^2$ | 0.15 W/in$^2$ |
| Weave | 0.20 W/in$^2$ | 0.15 W/in$^2$ | 0.15 W/in$^2$ | 0.15 W/in$^2$ |

TABLE I-continued

Vapour Deposition Plated Acticoat

| Plate Side | 1.70 W/in² | 1.50 W/in² | 1.40 W/in² | 1.20 W/in² |
|---|---|---|---|---|
| Non-Plated Side | 2.20 W/in² | 2.10 W/in² | 1.80 W/in² | 1.50 W/in² |

Silver Phosphate Glass Powder in Adhesive Arglaes[a]

| Adhesive Side | Infinite |
|---|---|

Silver Plated Ion Beam Technology Spi-Argent[a]

| Silver Catheter | Infinite |
|---|---|

Silver Leaf Preparation

| Silver Leaf | 0.20 W/in² | 0.20 W/in² | 0.20 W/in² | 0.20 W/in² |
|---|---|---|---|---|

99.99% Pure Solid Silver Sheet 100 μm thick

| Silver Sheet | 0.18 W/in² | 0.18 W/in² | 0.16 W/in² | 0.10 W/in² |
|---|---|---|---|---|

99.99% Pure Solid Silver Wire 1/16th inch thick

| Silver Wire | 0.10 W/in² |
|---|---|

99.99% Pure Solid Silver Screen with 0.05 mm Wires

| Silver Wire | 0.10 W/in² |
|---|---|

Mediskin I + Silver

| Procine Skin/Silver | 50 KW/in² | 50 KW/in² | 50 KW/in² | 50 KW/in² |
|---|---|---|---|---|

Tricot Jersey Knit Autocatylitic Plated Silver Nylon .9 ounces silver/m²
24 hours soaked in Normal Saline

| Measurement 24 hours soaked in Normal Saline | 1 Layer | 2 Layers: sewn | 3 Layers: sewn | 4 Layers: sewn |
|---|---|---|---|---|
| | 3.0 W/in² | 1.6 W/in² | 1.0 W/in² | 0.40 W/in² |
| 24 hours on human wound with silver nylon against the wound surface | 30.0 W/in² | 15.0 W/in² | 8.0 W/in² | 2.0 W/in² |

Bacteriology and Biological Reaction of Multi-ply Silver Conductive Layer Dressings When there is direct contact between the autocatalyitic silver plated nylon layer and the wound surface, the oligodynamic action of silver is sufficient to provide enough silver ions to act as am antimicrobial. The following tests were performed to verify this statement.

Test 1: Kirby-Bauer Standard Antimicrobial Suseptibility Test

The Kirby-Bauer Standard Antimicrobial Suseptibility Test showed that the multilayer autocatalytic silver plated nylon was an effective antimicrobial agent for inhibiting bacterial growth. In this test the multilayer autocatalytic silver plated nylon was tested in broth cultures of selected organisms. The broth is inoculated onto the surface of a Mueller-Hinton agar plate in three different directions. The test sample is them centered on the agar surface and incubated at 35–37° C. for 16 to 18 hours. After incubation, the diameter of the growth free zone of complete inhibition including the diameter of the disc is measured to the nearest whole millimeter. The resultant zone of inhibition is a qualitative indication of antimicrobial activity. Studies were preformed by independent NAMSA of Kenesaw, Ga.

| Test Organism | Results (Zone width − Sample width)/2 |
|---|---|
| S.aureus ATCC 33591 | 2 mm inhibition of growth under sample |
| S.aureus ATCC 6538 | 2 mm inhibition of growth under sample |
| P. aeruginosa ATCC 9027 | 2 mm inhibition of growth under sample |
| E. faecalis ATCC 51575 | 1 mm inhibition of growth under sample |

Test 2: Dow Corning Corporate Test Method 0923 Antimicrobial Activity-Dynamic Test of Surfaces The Dow Corning Corporate Test Method 0923 Antimicrobial Activity-Dynamic Test of Surfaces is a technique to screen the effectiveness of an antimicrobial agent applied to the surface of a textile. The method measures the antimicrobial activity of a treated textile by shaking a sample in 1.0–2.0×104 CFU/ml of a bacterial suspension for one hour contact time. The suspension is diluted before and after contact to determine bacterial counts. Study was preformed by an independent lab NAMSA of Kenesaw Ga.

TABLE 2

| | Organism Count (CFU/ml) | | |
|---|---|---|---|
| Test Organism | Zero Time | One Hour | Percent Reduction |
| S. Aureus ATCC6538 | 10,000 | <10 | 99.90 |
| P.aeruginosa ATCC 9027 | 27,000 | <10 | 99.96 |

Test 3: Assessment of Antibacterial Finishes on Textiles Material AATCC Test Method 100 (Modified)

The Assessment of Antibacterial Finishes on Textiles Material AATCC Test Method 100 (Modified) is a test method that determines whether the antimicrobial surface is effective or bactericidal and is recorded in percent of bacteria killed. A 4.8 cm disc of multilayer autocatalytic silver plated nylon is innoculated with $1-2\times10^5$ CFU of S. aureus and P. aeruginosa. The percent of bacterial reduction is determined from the counts taken at zero time and after 24 hours incubation. The study was preformed by an independent lab NAMSA of Kenesaw Ga.

TABLE 3

| Bacterial Species | Results in CFU/ml | | |
|---|---|---|---|
| | Zero Contact Time | 24 Hr. Contact Time | Percent Reduction |
| S.aureus | $1.4 \times 10^5$ | $<1.0 \times 10^2$ | 99.93 |
| P. aeruginosa | $2.7 \times 10^5$ | $<1.0 \times 10^2$ | 99.97 |

Test 4: Antimicrobial Effectiveness Test

The object of the antimicrobial effectiveness test is to demonstrate the level of effectiveness of the antimicrobial surface. Twenty grams of autocatalytic plated silver nylon is aseptically placed in 200 cc of normal saline and inoculated with the appropriate amount of inoculum suspension to obtain a population between $10^5$ and $10^6$ CFU/ml. After inoculation (day 0), the number of viable microorganisms for each organism will be determined by the standard plate count method using TSP for plating the bacterial organisms and SDA or PDA for plating fungal organisms. Test preparations are stored at 20° C.–25° C. for a period of 28 days. Aliquots from each of the inoculated test preparations are plated at 7, 14 ,21, and 28 days post inoculation to determine by standard plate count method using TSA and SDA or PDA. Sterile 0.9% saline or letheen broth will be used as a diluent. All bacteria plates will be incubated at 30° C. to 35° C. for 3 days; fungal plates are incubated at 20° C. S 25° C. for five days. Study was preformed by an independent lab NAMSA of Kenesaw Ga.

TABLE 4

| Multilaminate Autocatalytic Plated Silver Nylon | | | | | |
|---|---|---|---|---|---|
| | S. aureus ATCC 9027 | P. aeruginosa ATCC 8739 | E. coli ATCC 6538 | C. albicans ATCC 10231 | A. niger ATCC 16404 |
| Count of Inoculum | $2.9 \times 10^7$ | $3.7 \times 10^7$ | $5.1 \times 10^7$ | $9.5 \times 10^7$ | $2.4 \times 10^7$ |
| Calculated Organisms per g of Product | $1.5 \times 10^5$ | $1.9 \times 10^5$ | $2.6 \times 10^5$ | $4.8 \times 10^5$ | $1.2 \times 10^5$ |
| Day 0 | $2.0 \times 10^3$ | $2.0 \times 10^4$ | $2.0 \times 10^5$ | $2.1 \times 10^5$ | $5.0 \times 10^4$ |
| Day 7 | <10 | <10 | <10 | <10 | <10 |
| Day 14 | _ | 0 | 0 | 0 | 0 |
| Day 21 | 0 | 0 | 0 | 0 | 0 |
| Day 28 | 0 | 0 | 0 | 0 | 0 |

The result of Test 4 clearly shows that the multilaminate autocatalytic plated silver nylon is extremely effective as an antimicrobial surface in providing a sustained release of silver for antimicrobial activity. Study was performed by independent lab NAMSA of Kenesaw, Ga.

Test 5: ISO Sensitization Study in the Guinea Pig

In order to demonstrate that the autocatylitic silver plated nylon conductive layer 114 does not react adversely with the skin or surrounding body environment, a guinea pig maximization test of the multilaminate autocatalytic plated silver nylon was performed to look for delayed dermal contact sensitization. The multilaminate autocatalytic plated silver nylon was extracted in 0.9% sodium chloride USP (SC) and cottonseed oil, NF (CSO). Each extract was intradermally injected and occlusively patched to ten test guinea pigs (per extract) in an attempt to induce sensitization. The vehicle was similarly injected and osslusively patched to five control guinea pigs (per vehicle). Following a recovery period, the test and control animals received a challenge patch of the appropriate test article extract and the reagent control. In addition the test article was applied to the same animal. All sites were scored at 24, 48, and 72 hours after patch removal. Under these conditions, the SC and CSO test article extracts and the test article showed no evidence of dermal contact sensitization in the guinea pig. Study was performed by independent lab NAMSA of Kenesaw, Ga.

Chemical Analysis of the Autocatalytic Plated Silver Nylon

The autocatalytic plated silver nylon layer 114 was subjected to the following tests:

(1) Electron microscopy: reveals a uniform circumferential coating between 0.8 µm and 1.0 µm thick.

(2) X-ray Diffraction Spectrometry (XRD): reveals the composition of the coating to be 99% pure metallic silver and 1% silver oxide;

(3) Thermal gravimetric analysis of the silver plated surface: reveals no chemical residues from the plating process with only pure metallic silver.

Having set forth some of the testing results of the conductive layer 114, additional embodiments of the present invention shall be described in conjunction with FIGS. 32–47.

Figure 33:
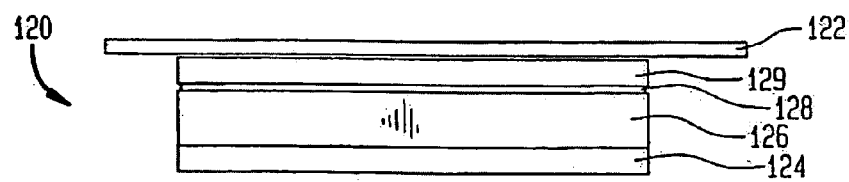

FIG. 33 shows a dressing 120 having the same laminar composition as the dressing 110 shown in FIG. 32 with the exception of the addition of highly conductive layer 129 that may be pure metal, combinations of metals, or metal coated fibers similar to layer 124 or 114. Dressing 120 also includes absorbent layer 126 and semi-permeable layer 128.

Figure 34:
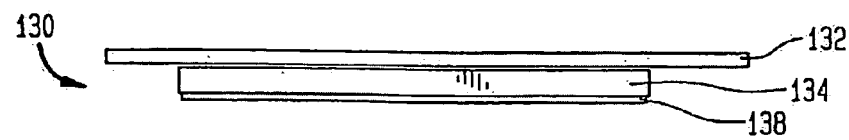

The dressing 130 of FIG. 34 is appropriate for application to a brace, splint or orthopaedic appliance and includes adhesive bandage 132, conductive layer 134 and semipermeable layer 138. Layer 132 is optional depending on the manner in which the dressing is affixed to the orthopaedic device.

Figure 35:
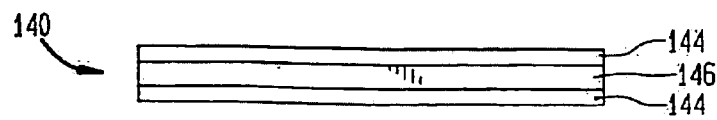

FIG. 35 shows a multilayer dressing/appliance 140 with two layers of conductive material, 144, separated by a layer of absorbent material, 146. The preferred absorbent material is a urathane foam. The specific application of dressing 140 is described below in reference to FIGS. 7 and 8.

Figure 36:
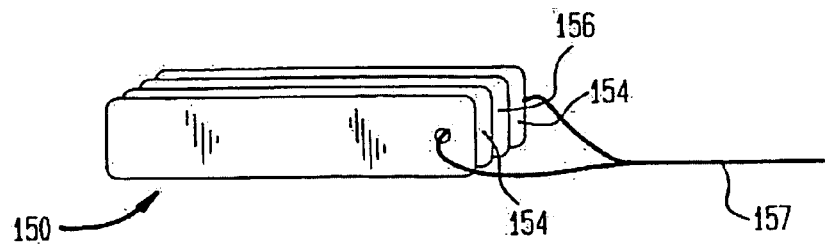
FIG. 36 shows a fifteenth embodiment of the present invention with the laminar dressing formed into a configuration for packing body cavities.

FIG. 36 shows the multilaminate material of FIG. 35 formed into the shape of a packing 150 for body cavities, e.g., nasal, auditory canal, vagina. As noted in reference to FIG. 35, the packing 150 has an absorbent layer 156 sandwiched between two conductive layers 154. A string 157 is provided to assist removal of the packing 150.

Figure 37:
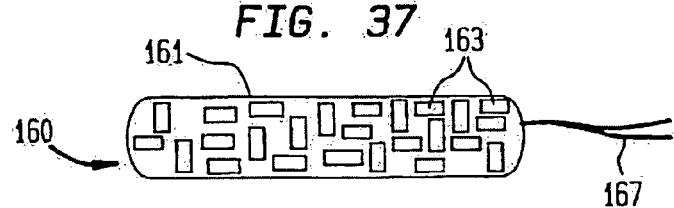
FIG. 37 shows a sixteenth embodiment of the present invention for packing a body cavity.

FIG. 37 shows a cavity packing 160 having a flexible, porous, outer sack 161 which contains a multitude of small cubes or chunks 163 of the tn-layer material 140 shown in FIG. 35. A pliable sack 161 allows the chunks 163 to conform to irregular cavities. A string 167 is provided for removal of the packing 160 and may also be employed as a cinch to close sack 161.

Figure 38:
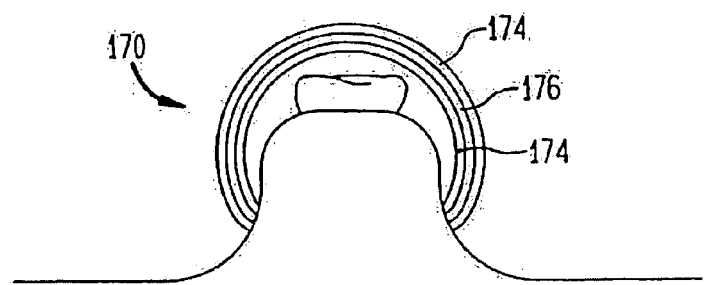
FIG. 38 is a schematic cross-sectional view of a seventeenth embodiment of the present invention for covering and treating a tooth and surrounding gum.

FIG. 38 shows a covering 170 for one of more teeth formed from the multilayer material 140 shown in FIG. 35. Preferably, the absorbent material selected has elastic memory to conform to the dimensions of the tooth and gum. Alternatively, the conductive layers 174 and the absorbent layer 176 may be selected to yield a deformable dressing that will take a set, e.g., when pressed into contact with the tooth and gum by a dentist.

Figure 39:
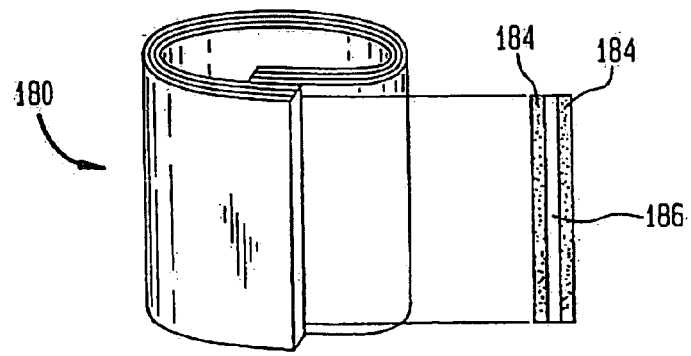
FIG. 39 is an elevational view of an eighteenth embodiment of the present invention wherein the laminar material of the present invention is formed into a tube shape.

FIG. 39 shows a tube 180 fabricated from material 140. The tube may be provided with elastic memory for use in surrounding generally cylindrical objects.

Figure 40:
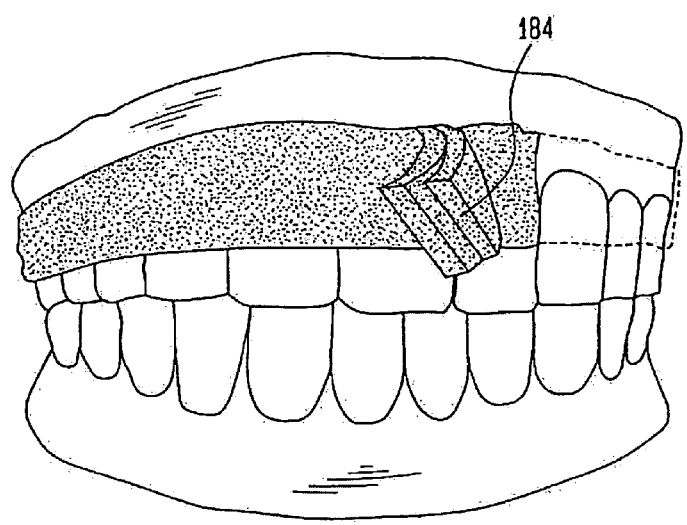
FIG. 40 is a schematic perspective view of a nineteenth embodiment of the present invention involving the application of the laminar material of the present invention to the gingival tissue on the buccal surface.

FIG. 40 shows a multi-ply silver nylon conductive layer 184 placed against the gingival tissue on the buccal surface. This dressing may be held in place by insertion between the lip and gum, by wiring or adhesives.

Figure 41:
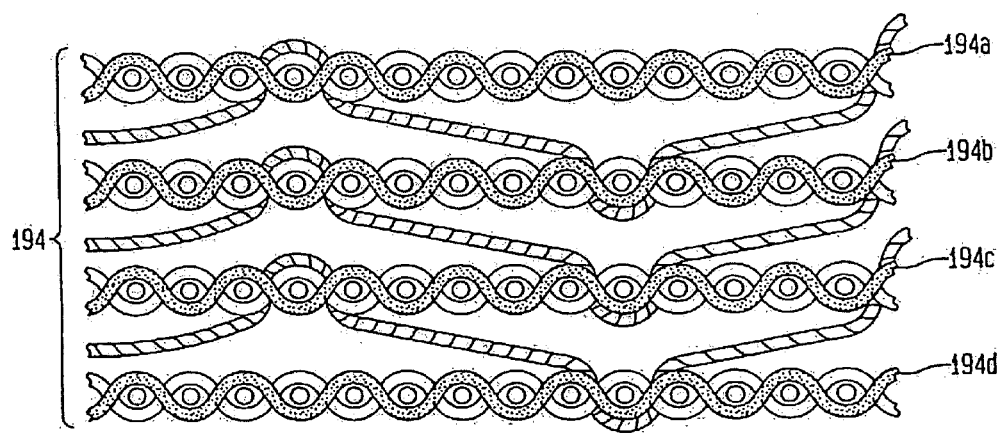
FIG. 41 is a diagrammatic cross-sectional view of the conductive layer in accordance with a twentieth embodiment of the present invention.

FIG. 41 shows schematically how four plies of silver nylon 194a–194d may be woven together to form a unitary multi-ply conductive layer 194.

Figure 42:
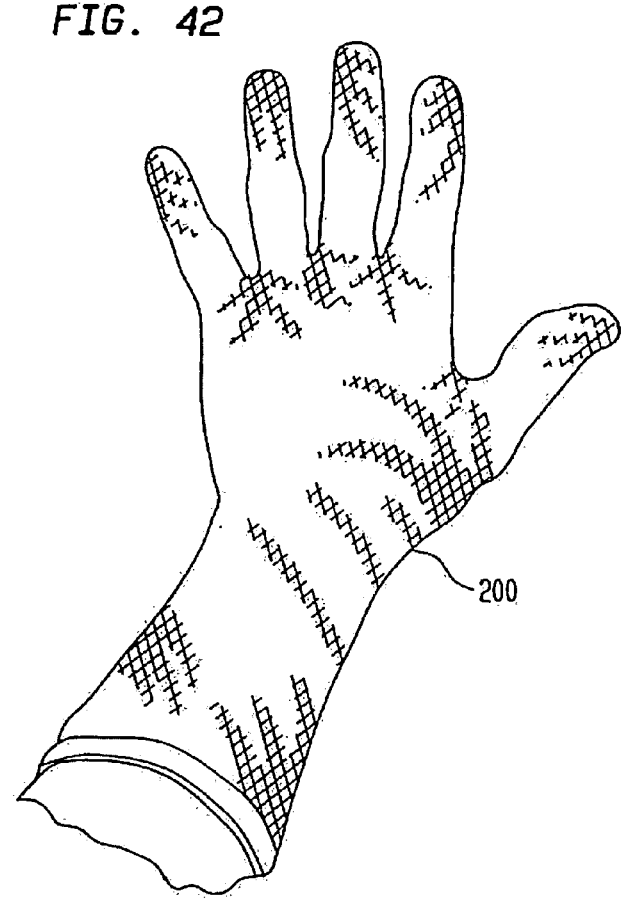
FIG. 42 shows a perspective view of a twenty-first embodiment of the present invention wherein the multi laminate material of the present invention is formed into a glove.

FIG. 42 shows a glove 200 formed from the material 190 shown in FIG. 41. The conductive layer 194 of the present invention can be used for healing and analgesia of osteoarthritis.

Figure 43:
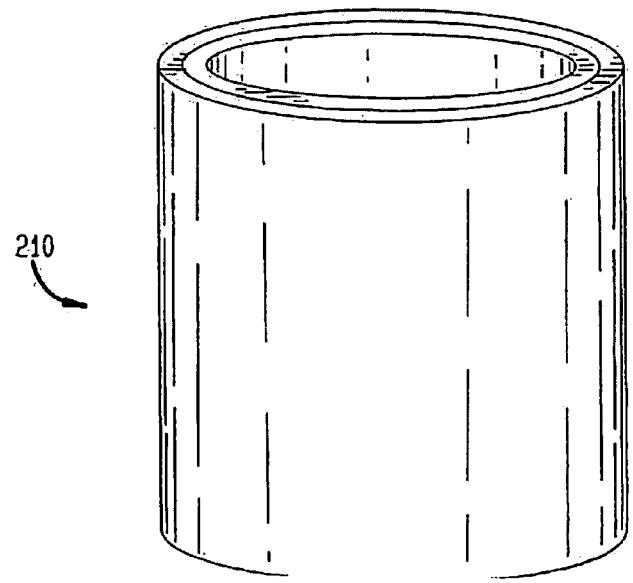
FIG. 43 is a schematic perspective view of a twenty-second embodiment of the present invention wherein a tubular wound drain is formed from the multilaminate material of the present invention.

FIG. 43 shows a wound drain 210 that is a multi-ply tube made from silver nylon. Any number of conductive layers may be employed, i.e., in concentric cylinders, which may be interleaved with absorbent layers.

Figure 44:
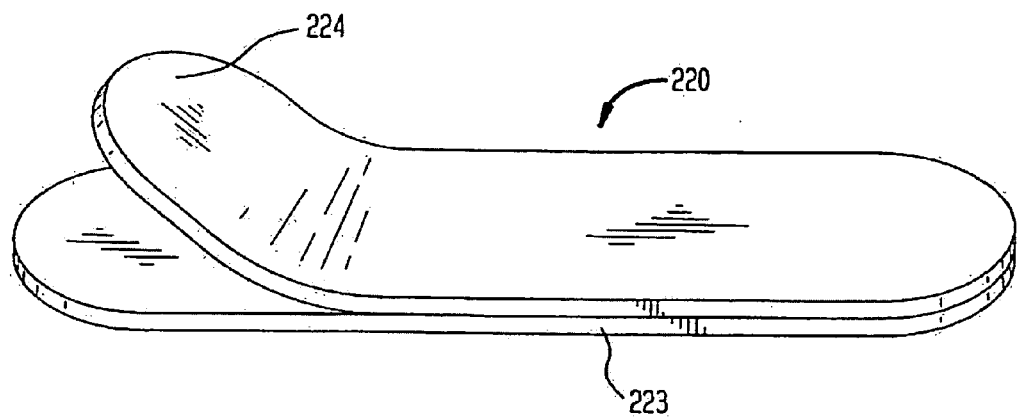
FIG. 44 is a perspective view of a twenty-third embodiment of the present invention wherein the multilaminate material is formed into a foot orthotic.

FIG. 44 shows a foot orthotic 220 with a layer of foam 223 and a layer of highly conductive silver nylon 224. Alternatively, the foam layer 223 could be positioned on the bottom and the conductive layer 224 on top. As a further alternative, the conductive layer 224 may be sandwiched between two layers of foam 223.

Figure 45:
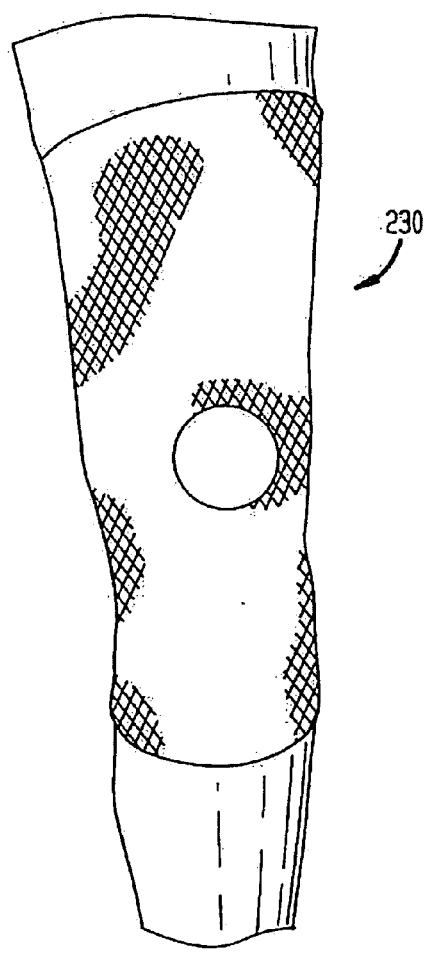
FIG. 45 is a perspective view of a knee sleeve formed from the material of the present invention.

FIG. 45 shows a knee sleeve 230 formed from at least one conductive layer 194, e.g., as shown in FIG. 41.

Clinical Findings

Clinical Data

Clinical evaluation of the analgesic effect of the dressing was conducted utilizing a visual analogue scale (VAS). (see *Methodological Problems in the Measurement of Pain:A comparison between the verbal rating scale and the Visual Analogue Scale,* Ohnhaus, E. E., and Adler, R., Pain 1 (1975), Page: 379–384 Elsevier/North-Holland, Amsterdam). The visual analogue scales are useful for measuring pain relief; the values correlate well with those for measuring pain intensity.( See *Studies with Different Types of Visual Analogue Scales for Measurement of Pain,* Sriwatanakui K, et ali., Clin. Pharmacol. Ther., August 1983 page 234–239). The patients were instructed to mark along a linear scale 10 cm long according to their interpretation of the pain intensity (Enclosure 1). New VAS sheets were presented to the patient at each of four evaluation points. The far left at the start of the line was no pain and the far right was agonizing pain (pain as bad as it could be) with the inbetween positions on the line progressing from little to mild to moderate to severe. The lines were measured and rounded to the nearest cm. So that the patients would act as their own controls, four readings were taken. The first reading was the level of pain on presentation to the physician with the medical problem untreated. A four ply laminate dressing in accordance with the present invention was applied and a VAS was noted at approximately 30 minutes. The dressing was then removed and a standard non-conductive dressing applied for ten minutes and the VAS recorded. The non-conductive dressing was than removed and the four ply laminate dressing was reapplied. After 30 minutes the patient marked the final VAS. The four VAS data points is called protocol 1.

The clinical cases reported cover a wide spectrum of pathologic states, including bone fractures, soft tissue contusions, ligament sprains, muscle strains, 2 week post surgical incision pain syndrome, and a variety of acute dermal lesions. In all cases, the four layer laminate dressing significantly reduced the patients perception of pain.

Case Studies

Open Acute Laceration

A 34 year old male presented with an acute laceration on the distal phalanx of his middle finger. The laceration was caused by a piece of sheet metal and extended across the tip of the digit to the tuft of the distal phalanx, measuring approximately 2 cm in length. The laceration was sharp with little soft tissue loss. The wound was inspected carefully and a four layer silver dressing applied in the office. Protocol 1 was initiated and findings recorded in Table 5. The patient was not placed on antibiotics. The four ply silver dressing was left in place for four days and than changed.

When the patient returned to the clinic in a week, the wound was healed without evidence of infection or nerve damage. The patient noted that as long as he kept the four ply silver dressing in place he had very little pain.

Acute Open Abrasion

A 52 year old male suffered a partial thickness abrasion to the anterior aspect of his knee after slipping on a cement sidewalk. The abrasion was partial thickness measuring approximately six cm in diameter. The four ply silver dressing was applied in the office. Protocol 1 was initiated and findings recorded in Table 5. The four ply silver dressing was left in place for three days, after which time a dressing was not required. When the patient returned to the clinic in a week, the wound was healed without evidence of infection. The patient noted that as long as he kept the four ply silver dressing in place he had very little pain.

Partial Thickness Burn

A five year old female suffered a partial thickness burn as a result of over exposure to sunlight on the dorsal aspects of her feet bilaterally. At the time the patient was seen, the dorsal aspect of the feet were edematous and extremely painful to any pressure. The four ply silver dressing was applied. Protocol 1 was initiated and findings recorded in Table 5. The four ply silver dressing was left in place for three days, after which time a dressing was not required. When the patient returned to the clinic in a week, the wound was healed without evidence of any skin changes. The patient noted that as long as he kept the four ply silver dressing in place he had very little pain.

Two Weeks After Wound Closed

A 48 year old male presented with a painful scar two weeks after a surgical repair of an inguinal hernia. Upon examination the surgical scar was well healed. The four ply silver dressing was applied to skin surrounding the surgical scar. Protocol 1 was initiated and findings recorded in Table 5. The four ply silver dressing was left in place for seven days. When the patient returned to the clinic in three weeks, the surgical scar was pain free.

Ankle Sprain

A 36 year old male presented with an acute ankle sprain of the lateral ligamentous complex. X-rays revealed no fractures and on physical examination the problem was limited to the lateral ligamentous complex: the anterior inferior tib-fib ligament and the anterior fibulotalar ligament.

Table 5. The four ply silver dressing was left in place for three weeks, changing the dressing every seven days. By the end of the third week, x-rays revealed excellent callus formation at the fracture site. At this time the patients stated that he was pain free. The brace and dressing was discontinued. The patient returned to the clinic in three additional weeks to report that he was pain free. His physical examination was normal without tenderness over the fracture site. He was discharged from the inventor's care at that time.

Clinical Case Studies

TABLE 5

| Wound or Injury Category | Initial Plain (1) | 30 Min. After Application (2) | 10 Min. After Removal (3) | 30 Min. After Final Application (4) |
|---|---|---|---|---|
| Post Surgical Wound | | | | |
| Open Acute Laceration | 8 | 1 | 8 | 1 |
| Open Acute Abrasion | 7 | 1 | 6 | 0 |
| Open Acute Partial Thickness Burn | 9 | 1 | 8 | 1 |
| 2 Weeks After Wound Closed | 6 | 0 | 6 | 0 |
| Sprains/Strains | | | | |
| Ankle Sprain | 8 | 1 | 7 | 1 |
| Intercostal Muscle Strain Contusion | 6 | 2 | 6 | 1 |
| Lower Extremity Fracture | 8 | 1 | 7 | 1 |
| Metatarsal Fracture | 7 | 1 | 7 | 1 |

The four ply silver dressing was applied. Protocol 1 was initiated and findings recorded in Table 5. The four ply silver dressing was left in place for fourteen days under a compressive bandage. When the patient returned to the clinic in two weeks, the ecchymosis and tenderness to palpation over the lateral ligamentous complex was absent. At the time the patient had a negative talor tilt test and a negative anterior draw sign. He had full range of motion of the ankle joint with no discomfort.

Intercostal Muscle Strain

The patient is a 47 year old female who suffered blunt trauma to the anterior lateral thoracic region between the 6th and the 9th ribs mid axillary line. Seven days after the blunt trauma the patient was seen in the clinic with exquisite tenderness in the mid axillary line between the 6th and 9th ribs. Chest x-ray was negative for fracture or pulmonary contusion. The four ply silver dressing was applied under a rib belt. Protocol 1 was initiated and findings recorded in Table 5. The four ply silver dressing was left in place for ten days. In two weeks the patient called the office to cancel her appointment due to the fact that she was pain free and had no complaints. The patient noted that as long as she kept the four ply silver dressing in place she had very little pain.

Metatarsal Fracture

The patient is a 56 year old male who suffered a fifth metatarsal fracture secondary to a fall. The fracture pattern was a spiral oblique without comminution. The injury was closed. The four ply silver dressing was applied under a compressive dressing and the foot was placed in a fracture brace. Protocol 1 was initiated and findings recorded in Visual Analogue Pain Scale and Instructions The VAS Scale is simply a horizontal line that is accompanied by the following instructions.

"Place one mark on the line drawn below to indicate the level of pain that you are currently experiencing at this moment. The far left at the start of the line represents no pain while the far right represents agonizing pain (pain as bad as it could be) with the inbetween positions on the line progressing from little to mild to moderate to severe."

Although only a few exemplary embodiments of this invention have been described in detail above, those skilled in the art will readily appreciate that many modification are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures.

It should further be noted that any patents, application or publications referred to herein are incorporated by reference in their entirety.

The invention claimed is:

1. A method for promoting healing of a pathology comprising:
    passively modulating the pathology's electrical potential to about −10 to about −70 mV by conductively bridging healthy tissue surrounding the pathology, wherein the alternation in the pathology's electrical potential promotes healing of the pathology.

2. The method of claim 1, wherein the pathology's electrical potential is lowered.

3. The method of claim 1, wherein the healthy tissue surrounding the pathology is conductively bridged by applying a conductive substrate.

4. The method of claim 3, wherein the conductive substrate comprises a metalized fiber.

5. The method of claim 4, wherein the conductive substrate further comprises a nonmetalized fiber.

6. The method of claim 4, wherein the metalized fiber comprises a conductive metal.

7. The method of claim 6, wherein the conductive metal is silver.

* * * * *

UNITED STATES PATENT AND TRADEMARK OFFICE
CERTIFICATE OF CORRECTION

PATENT NO. : 7,291,762 B2  Page 1 of 1
APPLICATION NO. : 10/660209
DATED : November 6, 2007
INVENTOR(S) : A. Bart Flick It is certified that error appears in the above-identified patent and that said Letters Patent is hereby corrected as shown below:

Title page of the patent, Item (63), replace "continuation of application no. 09/531,245, filed on March 21, 2000, now Pat. No. 6,861,570, which is a continuation of application no. PCT/US98/19689, filed on September 22, 1998" with --continuation of application no. 09/531,245, filed on March 21, 2000, now Pat. No. 6,861,570, which is a continuation of application no. PCT/US98/19689, filed on September 22, 1998, which is a continuation-in-part of application no. 08/935,026, filed on September 22, 1997, now Pat. No. 6,087,549--.

Signed and Sealed this

Second Day of September, 2008

JON W. DUDAS
*Director of the United States Patent and Trademark Office*